(12) United States Patent
Sakaue

(10) Patent No.: US 9,662,083 B2
(45) Date of Patent: May 30, 2017

(54) MEDICAL IMAGE DISPLAY APPARATUS AND MEDICAL IMAGE DISPLAY SYSTEM

(71) Applicant: TOSHIBA MEDICAL SYSTEMS CORPORATION, Otawara-Shi (JP)

(72) Inventor: Kousuke Sakaue, Nasushiobara (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 14/672,813

(22) Filed: Mar. 30, 2015

(65) Prior Publication Data

US 2015/0294445 A1 Oct. 15, 2015

(30) Foreign Application Priority Data

Apr. 10, 2014 (JP) .................... 2014-081044

(51) Int. Cl.
*G06K 9/00* (2006.01)
*A61B 6/00* (2006.01)
*G06T 7/33* (2017.01)
*A61B 6/03* (2006.01)

(52) U.S. Cl.
CPC ............ *A61B 6/5247* (2013.01); *A61B 6/469* (2013.01); *G06T 7/33* (2017.01); *A61B 6/032* (2013.01); *A61B 6/037* (2013.01); *G06T 2207/10081* (2013.01); *G06T 2207/10088* (2013.01); *G06T 2207/10104* (2013.01); *G06T 2207/10108* (2013.01)

(58) Field of Classification Search
None
See application file for complete search history.

(56) References Cited

U.S. PATENT DOCUMENTS

| | | | |
|---|---|---|---|
| 6,175,655 B1* | 1/2001 | George, III | G06F 19/321 358/451 |
| 8,150,132 B2 | 4/2012 | Nakamura | |
| 2006/0229513 A1* | 10/2006 | Wakai | G06T 5/50 600/407 |
| 2006/0239524 A1* | 10/2006 | Desh | G06F 19/321 382/128 |

(Continued)

FOREIGN PATENT DOCUMENTS

| | | |
|---|---|---|
| JP | 2008-194456 | 8/2008 |
| JP | 2009-219655 | 10/2009 |

(Continued)

*Primary Examiner* — Shervin Nakhjavan
(74) *Attorney, Agent, or Firm* — Oblon, McClelland, Maier & Neustadt, L.L.P.

(57) ABSTRACT

A medical image display apparatus for displaying at least one medical image acquired from an object, the medical image display apparatus comprises: memory circuitry configured to store at least one functional image representing functional information of a tissue in the object, and at least one morphological image representing morphological information of the object; processing circuitry configured: to specify a region of interest based on the functional image; and to find a position of a characteristic structure of a human body by analyzing the morphological image, the position detection section being further configured to find area information corresponding to the position of the region of interest of the functional image; and a display configured to display the area information.

14 Claims, 19 Drawing Sheets

(56) References Cited

U.S. PATENT DOCUMENTS

| | | | |
|---|---|---|---|
| 2008/0170771 A1 | 7/2008 | Yamagata et al. | |
| 2008/0273775 A1* | 11/2008 | Hilbelink | G06T 7/0012 |
| | | | 382/128 |
| 2008/0319331 A1* | 12/2008 | Zizzo | A61B 5/04012 |
| | | | 600/511 |
| 2009/0010519 A1* | 1/2009 | Wakai | G06F 19/321 |
| | | | 382/131 |
| 2009/0135992 A1* | 5/2009 | Vaillant | G06T 7/0038 |
| | | | 378/4 |
| 2009/0232378 A1 | 9/2009 | Nakamura | |
| 2010/0217116 A1* | 8/2010 | Eck | A61B 6/463 |
| | | | 600/424 |
| 2012/0063663 A1* | 3/2012 | Kawasaki | G06T 7/0014 |
| | | | 382/133 |
| 2013/0044927 A1 | 2/2013 | Poole | |
| 2014/0003700 A1* | 1/2014 | Hermosillo Valadez | G06T 11/003 |
| | | | 382/131 |
| 2014/0153804 A1* | 6/2014 | Jattke | G06T 7/0012 |
| | | | 382/131 |
| 2014/0187902 A1* | 7/2014 | Sato | A61B 5/0095 |
| | | | 600/407 |

FOREIGN PATENT DOCUMENTS

| | | |
|---|---|---|
| JP | 2013-039344 | 2/2013 |
| JP | 5138431 | 2/2013 |
| JP | 5197029 | 5/2013 |
| WO | WO 2008/081365 A2 | 7/2008 |

\* cited by examiner

FIG. 5A

| HEAD, NECK |
|---|
| ANTERIOR ARCH (TUBERCLE) OF ATLAS (CERVICAL VERTEBRA I) |
| SUPERIOR TIP OF DENS / PEG (CERVICAL VERTEBRA II) |
| SUPERIOR ASPECT OF RIGHT EYE GLOBE |
| SUPERIOR ASPECT OF LEFT EYE GLOBE |
| CENTER OF RIGHT EYE GLOBE |
| CENTER OF LEFT EYE GLOBE |
| ⋮ |

FIG. 5B

| CHEST |
|---|
| BIFURCATION OF TRACHEA |
| APEX OF RIGHT LUNG |
| APEX OF LEFT LUNG |
| INFERIOR ANGLE OF RIGHT SCAPULA |
| INFERIOR ANGLE OF LEFT SCAPULA |
| START OF LEFT SUBCLAVIAN ARTERY (BRANCHING OFF AORTIC ARCH) |
| ⋮ |

FIG. 5C

| ABDOMEN |
|---|
| SUPERIOR POLE OF RIGHT KIDNEY |
| SUPERIOR POLE OF LEFT KIDNEY |
| INFERIOR POLE OF RIGHT KIDNEY |
| INFERIOR POLE OF LEFT KIDNEY |
| HEAD OF PANCREAS |
| TIP OF TAIL OF PANCREAS |
| ⋮ |

FIG. 5D

| LOWER LIMBS |
|---|
| LATERAL EPICONDYLE OF RIGHT FEMUR |
| MEDIAL EPICONDYLE OF RIGHT FEMUR |
| LATERAL EPICONDYLE OF LEFT FEMUR |
| MEDIAL EPICONDYLE OF LEFT FEMUR |
| LATERAL CONDYLE OF RIGHT TIBIA |
| MEDIAL CONDYLE OF RIGHT TIBIA |
| ⋮ |

| IDENTIFIER | NAME | RELIABILITY | PART | BODY TISSUE | PATIENT COORDINATE SYSTEM | | |
|---|---|---|---|---|---|---|---|
| | | | | | X | Y | Z |
| ABD025.C | CENTER OF BODY OF L5 | 0.87 | ABDOMEN | SKELETAL SYSTEM | -3.1 | 23.4 | 90.0 |
| ABD032.C | SUPERIOR ASPECT OF RIGHT ILIAC SPINE | 0.82 | ABDOMEN | SKELETAL SYSTEM | -11.1 | -54.4 | 84.1 |
| ABD039.C | SUPERIOR ASPECT OF LEFT ILIAC SPINE | 0.83 | ABDOMEN | SKELETAL SYSTEM | -3.0 | 30.0 | 104.0 |
| ⋮ | ⋮ | ⋮ | ⋮ | ⋮ | ⋮ | ⋮ | ⋮ |

| REGION OF INTEREST | FUNCTIONAL ABNORMALITY POSITION | PART | BODY TISSUE | ORGAN | ... |
|---|---|---|---|---|---|
| REGION OF INTEREST 1 | AL2 | CHEST | RESPIRATORY SYSTEM | LEFT LUNG | ... |
| REGION OF INTEREST 2 | AL5 | ABDOMEN | DIGESTIVE SYSTEM | LIVER | ... |
| ⋮ | ⋮ | ⋮ | ⋮ | ⋮ | ... |

PAST FUSION IMAGE DATA

| REGION OF INTEREST | FUNCTIONAL ABNORMALITY POSITION | PART | BODY TISSUE | ORGAN | ... |
|---|---|---|---|---|---|
| REGION OF INTEREST 1 | AL2 | CHEST | RESPIRATORY SYSTEM | LEFT LUNG | ... |
| REGION OF INTEREST 2 | AL5 | ABDOMEN | DIGESTIVE SYSTEM | LIVER | ... |
| | AL6 | ABDOMEN | DIGESTIVE SYSTEM | LIVER | ... |

FIG. 16A

LATEST FUSION IMAGE DATA A

| REGION OF INTEREST | FUNCTIONAL ABNORMALITY POSITION | PART | BODY TISSUE | ORGAN | ... |
|---|---|---|---|---|---|
| REGION OF INTEREST 1 | AL2 | CHEST | RESPIRATORY SYSTEM | LEFT LUNG | ... |
| REGION OF INTEREST 2 | AL5 | ABDOMEN | DIGESTIVE SYSTEM | LIVER | ... |

FIG. 16B

LATEST FUSION IMAGE DATA B

| REGION OF INTEREST | FUNCTIONAL ABNORMALITY POSITION | PART | BODY TISSUE | ORGAN | ... |
|---|---|---|---|---|---|
| REGION OF INTEREST 1 | AL1 | CHEST | RESPIRATORY SYSTEM | LEFT LUNG | ... |
| | AL2 | CHEST | RESPIRATORY SYSTEM | RIGHT LUNG | ... |
| REGION OF INTEREST 2 | AL5 | ABDOMEN | DIGESTIVE SYSTEM | LIVER | ... |
| | AL6 | ABDOMEN | DIGESTIVE SYSTEM | LIVER | ... |
| REGION OF INTEREST 3 | AL7 | ABDOMEN | URINARY SYSTEM | LEFT KIDNEY | ... |

FIG. 16C

PAST FUSION IMAGE DATA

| REGION OF INTEREST | FUNCTIONAL ABNORMALITY POSITION | VOLUME (mm$^3$) |
|---|---|---|
| REGION OF INTEREST 1 | AL2 | 15 |
| REGION OF INTEREST 2 | AL5 | 30 |
| | AL6 | |

FIG. 17A

PAST FUSION IMAGE DATA A

| REGION OF INTEREST | FUNCTIONAL ABNORMALITY POSITION | VOLUME (mm$^3$) |
|---|---|---|
| REGION OF INTEREST 1 | AL2 | 8 |
| REGION OF INTEREST 2 | AL5 | 20 |

FIG. 17B

PAST FUSION IMAGE DATA B

| REGION OF INTEREST | FUNCTIONAL ABNORMALITY POSITION | VOLUME (mm$^3$) |
|---|---|---|
| REGION OF INTEREST 1 | AL1 | 60 |
| | AL2 | |
| REGION OF INTEREST 2 | AL5 | 90 |
| | AL6 | |
| REGION OF INTEREST 3 | AL7 | 15 |

FIG. 17C

LATEST FUSION IMAGE DATA A

| REGION OF INTEREST | FUNCTIONAL ABNORMALITY POSITION | VOLUME INCREASE/DECREASE (%) |
|---|---|---|
| REGION OF INTEREST 1 | AL2 | 53 |
| REGION OF INTEREST 2 | AL5 | 67 |

FIG. 18A

LATEST FUSION IMAGE DATA B

| REGION OF INTEREST | FUNCTIONAL ABNORMALITY POSITION | VOLUME INCREASE/DECREASE (%) |
|---|---|---|
| REGION OF INTEREST 1 | AL1 | 400 |
| | AL2 | |
| REGION OF INTEREST 2 | AL5 | 300 |
| | AL6 | |
| REGION OF INTEREST 3 | AL7 | – |

FIG. 18B

PAST FUSION IMAGE DATA

| REGION OF INTEREST | FUNCTIONAL ABNORMALITY POSITION | RI ACCUMULATION VALUE |
|---|---|---|
| REGION OF INTEREST 1 | AL2 | 25 |
| REGION OF INTEREST 2 | AL5 | 15 |
| | AL6 | |

FIG. 19A

LATEST FUSION IMAGE DATA A

| REGION OF INTEREST | FUNCTIONAL ABNORMALITY POSITION | RI ACCUMULATION VALUE | INCREASE/DECREASE (%) OF RI ACCUMULATION VALUE |
|---|---|---|---|
| REGION OF INTEREST 1 | AL2 | 10 | 40 |
| REGION OF INTEREST 2 | AL5 | 15 | 100 |

FIG. 19B

LATEST FUSION IMAGE DATA B

| REGION OF INTEREST | FUNCTIONAL ABNORMALITY POSITION | RI ACCUMULATION VALUE | INCREASE/DECREASE (%) OF RI ACCUMULATION VALUE |
|---|---|---|---|
| REGION OF INTEREST 1 | AL1 | 35 | 140 |
| | AL2 | | |
| REGION OF INTEREST 2 | AL5 | 25 | 167 |
| | AL6 | | |
| REGION OF INTEREST 3 | AL7 | 20 | — |

FIG. 19C

MEDICAL IMAGE DISPLAY APPARATUS AND MEDICAL IMAGE DISPLAY SYSTEM

CROSS-REFERENCE TO RELATED APPLICATION

This application is based upon and claims the benefit of priority from Japanese Patent Application No. 2014-81044, filed on Apr. 10, 2014, the entire contents of which are incorporated herein by reference.

FIELD

An embodiment as one aspect of the present invention relates to a medical image display apparatus and a medical image display system.

BACKGROUND

Various examination apparatuses for use in imaging diagnosis (hereafter, referred to as modality apparatuses) are indispensable in modern medical services since they allow examination of internal body in a minimally invasive manner. For example, a nuclear medicine diagnostic apparatus such as a SPECT (Single Photon Emission Computed Tomography) apparatus and a PET (Positron Emission Tomography) apparatus enables diagnosis of functions of organs and tissues. Such a nuclear medicine diagnostic apparatus detects gamma rays radiated from a radioactive medicine selectively incorporated in a living tissue of an object with a detector, and generates a nuclear medicine image from the dose distribution of the detected gamma rays. To be specific, the SPECT apparatus and PET apparatus generate projection data (sinogram data) from the dose distribution of gamma rays detected by the detector, and perform inverse projection processing of the generated projection data, thereby reconstructing a nuclear medicine image (SPECT image and PET image). For example, by using a medicine which accumulates only in cancers, it is possible to examine a metastasis lesion of cancer over the whole body. Moreover, it is also possible to examine the status of blood flow and blood circulation in the brain by using a medicine which accumulates in the brain in accordance with blood flow. However, although a nuclear medicine image has excellent functional information, it is rather lacking in anatomical and morphological information.

In the meantime, an image obtained by an X-ray CT (Computed Tomography) apparatus and an MRI (Magnetic Resonance Imaging) apparatus has high resolution, and provides a plenty of anatomical and morphological information of organs and tissues. Accordingly, by generating a fusion image in which a nuclear medicine image and a CT image or MRI image are fused together (synthesized), it becomes possible to put functional information and anatomical and morphological information together into one image and provide physicians with useful information in imaging diagnosis.

To make high quality diagnosis, it is necessary to appropriately grasp an abnormal area and treatment area from an acquired fusion image. However, reading out an anatomical area from a medical image requires experienced skills and knowledge. Accordingly, as an automated method for identifying and emphasizing a region which is potentially abnormal, various computer assisted detection (CAD) techniques have been developed. For example, a CAD system which specifies an abnormal structure through comparison with a template which has statistical information regarding abnormal areas has been provided. Moreover, as the invention for supporting imaging diagnosis, there are proposed a medical image processing apparatus which specifies anatomical areas by using a segmentation technique etc. and determining a region where abnormality exists and its malignancy, and an image analysis apparatus which determines the positional correlation of images acquired at two different examinations from a structure having a periodicity, such as a spine cord.

In recent years, provision of and study on a technique for representing and constructing anatomical positions of a human body by using a mathematical method have been conducted. The anatomical position means a position of a characteristic local structure of a human body (hereafter, simply referred to as a "local structure") which plays an important role in understanding medical images, and serves as a mark when mapping a human body in an anatomical fashion. For example, the local structure may be the anterior arch (nodule) of the first cervical vertebra (cervical vertebra I) in the head area, the bifurcation of the trachea in the chest area, and the upper pole of the right kidney in the abdomen area. The position of the local structure (anatomical position) is automatically detected by a general image analysis and pattern recognition technology, etc. from a medical image acquired by a modality apparatus such as an X-ray CT apparatus and an MRI apparatus.

As described above, in imaging diagnosis of nuclear medicine image, identifying an anatomical area in which abnormality is observed, from a fusion image in which a nuclear medicine image and a CT image or MRI image are fused together (synthesized) is generally difficult, and requires experienced skills. Therefore, it takes time to specify anatomical areas where abnormality is observed, which becomes a barrier against early diagnosis. In addition, due to recent improvements in image processing technology, there is a case where the fusion image to be acquired is a three-dimensional image. To specify an anatomical area where abnormality is observed from a three-dimensional fusion image, it is necessary to perform operations such as rotating the image, or continuously observing predetermined sections. Further, it is required to give detailed explanation to the patient on the cause of disease and the content of treatment, and there is need for a display method, etc. for providing explanation to the patient and others in an easy-to-understand manner.

Accordingly, there is need for a medical image display apparatus for easily confirming areas where abnormality is observed on a fusion image by using the above described positions of local structure (anatomical positions).

BRIEF DESCRIPTION OF THE DRAWINGS

In accompanying drawings,

FIGS. 5A to 5D are diagrams to explain kinds of local structures.

FIGS. 16A to 16C are diagrams to illustrate abnormal area lists of past and latest fusion images of the medical image display apparatus relating to an embodiment.

FIGS. 17A to 17C are diagrams to illustrate a first measurement result of past and latest fusion images of the medical image display apparatus relating to an embodiment.

FIGS. 18A and 18B are diagrams to illustrate a comparison result based on a first measurement result of past and latest fusion images of the medical image display apparatus relating to an embodiment.

FIGS. 19A to 19C are diagrams to illustrate a second measurement result and comparison result between past and latest fusion images of the medical image display apparatus relating to an embodiment.

DETAILED DESCRIPTION

Hereafter, embodiments of a medical image display apparatus will be described with reference to appended drawings.

A medical image display apparatus relating to an embodiment is a medical image display apparatus for displaying at least one medical image acquired from an object, which comprises: an image storage section configured to store at least one functional image representing functional information of a tissue in the object, and at least one morphological image representing morphological information of the object; an abnormal-area specification section configured to specify a region of interest based on the functional image; a position detection section configured to find a position of a characteristic structure of a human body by analyzing the morphological image, the position detection section being further configured to find area information corresponding to the position of the region of interest of the functional image; and a display section configured to display the area information.

(General Configuration)

Figure 1:
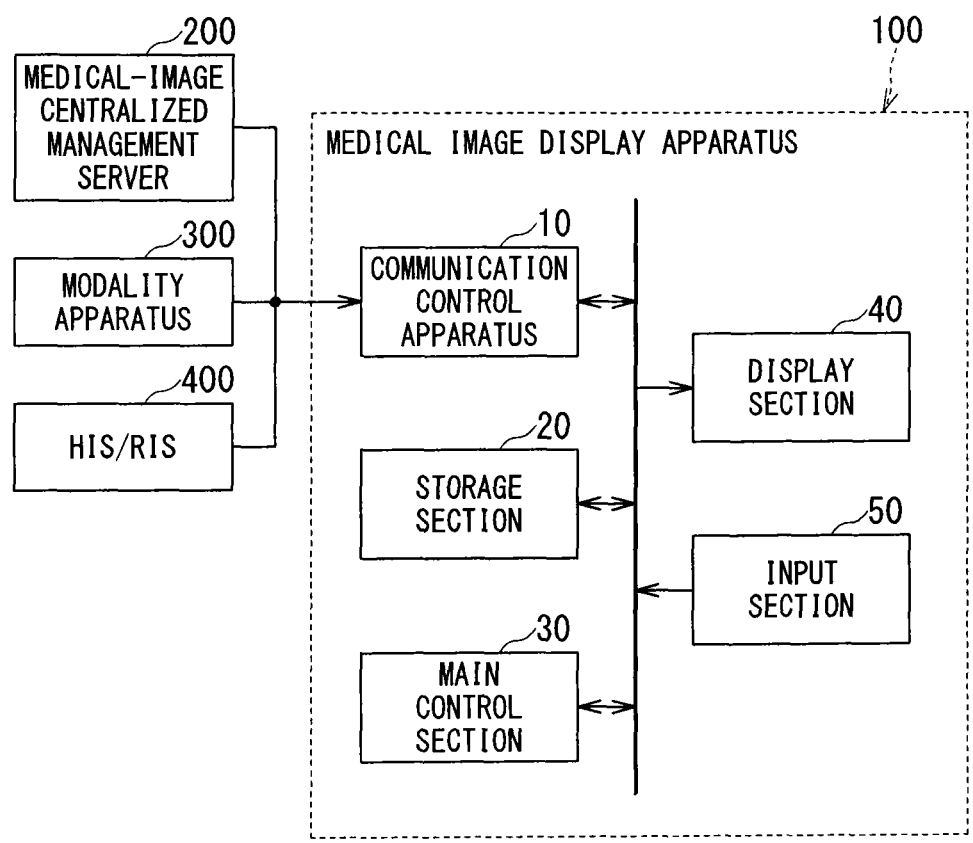
FIG. 1 is a conceptual block diagram to show an example of a medical image display apparatus relating to an embodiment.

FIG. 1 is a conceptual block diagram to show an example of a medical image display apparatus 100 relating to an embodiment. As shown in FIG. 1, the medical image display apparatus 100 includes a communication control apparatus 10, a storage section 20, a main control section 30, a display section 40 (display 40), and an input section 50 (input device 50). The medical image display apparatus 100 is connected to a medical-image centralized management server 200, a modality apparatus 300, and an HIS(Hospital Information System)/RIS(Radiology Information System) 400 via the communication control apparatus 10 over an electronic network. The communication control apparatus 10 implements various communication protocols according to network forms. Here, an electronic network means entire information communication networks utilizing electric communication technologies, and includes hospital backbone LANs, wireless/wired LANs, Internet networks as well as telecommunication networks, optical fiber communication networks, cable communication networks and satellite communication networks. The medical image display apparatus 100 acquires examination data over an electronic network from the medical-image centralized management server 200, which accumulates images acquired at the modality apparatus as electronic data, or the modality apparatus 300.

It is noted that the medical-image centralized management server 200, the HIS/RIS 400, and the medical image display apparatus 100 may be configured as a medical image display system on a cloud computing platform. In this case, the medical image display apparatus 100 of the medical image display system can acquire medical images over a network from, for example, the medical-image centralized management server 200 and the modality apparatus 300.

The modality apparatus 300 includes various modality apparatuses such as an X-ray CT (Computed Tomography) apparatus, an MRI (Magnetic Resonance Imaging) apparatus, a PET (Positron Emission Tomography) apparatus, or a SPECT (Single Photon Emission computed Tomography) apparatus.

Data to be inputted to the medical image display apparatus 100 is volume data made up of a plurality of images (for example, slice images). The medical image display apparatus 100 acquires a plurality of medical images each of which is made up of a plurality of images. Among medical images inputted to the medical image display apparatus 100, those acquired by an X-ray CT (Computed Tomography) apparatus, an MRI (Magnetic Resonance Imaging) apparatus, etc. will be referred to as "morphological images", and those acquired by a nuclear medicine diagnostic apparatus such a PET (Positron Emission Tomography) apparatus or a SPECT (Single Photon Emission Computed Tomography) apparatus as "functional images".

Moreover, the medical image display apparatus 100 is connected with a hospital system (HIS) or a radiology information system (RIS), which is an ordering system for processing examination requests from physicians over an electronic network. The HIS/RIS 400 is a system for processing examination requests, which are created by physicians and the like called as examination orders. From the HIS/RIS 400, it is possible to acquire, over an electronic network, patient information such as a patient ID for uniquely identifying the patient or a patient name, sexuality and physical features of the patient, and examination requests such as a treatment content, an examination type, an examination purpose, and a modality apparatus type. The treatment content will include types of medication and treatment which have been prescribed to the patient, previous history, and the like.

As the result of a program stored in the storage section 20 being executed by the main control section 30, assignment of a position of local structure (anatomical position) on acquired volume data, generation of a fusion image in which a morphological image and a functional image are fused together, specification of area information corresponding to a region of interest of a functional image, and the like are performed. It is noted that in the following description, a position in a patient coordinate system of a local structure which is detected from a medical image is conveniently referred to as an anatomical position.

The storage section 20 may be configured to include a storage medium, which is readable by the main control section 30, such as a magnetic or optical storage medium or a semiconductor memory including a RAM, ROM, or HDD (Hard Disk Drive) such that part or all of the program and data in these storage media can be downloaded over an electronic network. Moreover, assignment of an anatomical position performed in the medical image display apparatus 100 may be performed by using a program and data which are stored in advance in the storage section 20, or by using data etc. stored in an external storage apparatus via the communication control apparatus 10, or by a program stored in an external storage apparatus, etc.

The display section 40 is made up of a general display apparatus such as a liquid crystal display and an OLED (Organic Light Emitting Diode) display, and displays images according to the control by the main control section 30.

The input section 50 is made up of general input devices such as a keyboard, touch panel, ten key, and mouse. The input section 50 outputs input signals, which correspond to operations such as selection of image and selection of region of interest, to the main control section 30.

Hereafter, a method which includes generating a fusion image and specifying an anatomical area in which abnormality is observed (hereafter, referred to as an abnormal area) based on an anatomical position of the fusion image will be described as a "first embodiment", and a method which includes quantitatively analyzing the abnormal area, and comparing it with data acquired by a past examination, in addition to performing the first embodiment as a "second embodiment", respectively. Moreover, a method which includes generating a past fusion image and a latest fusion image respectively, thereafter specifying an anatomical position corresponding to respective regions of interest of the past fusion image and the latest fusion image, and displaying them in correspondence with each other will be described as a "third embodiment".

First Embodiment (1) Configuration

Figure 2:
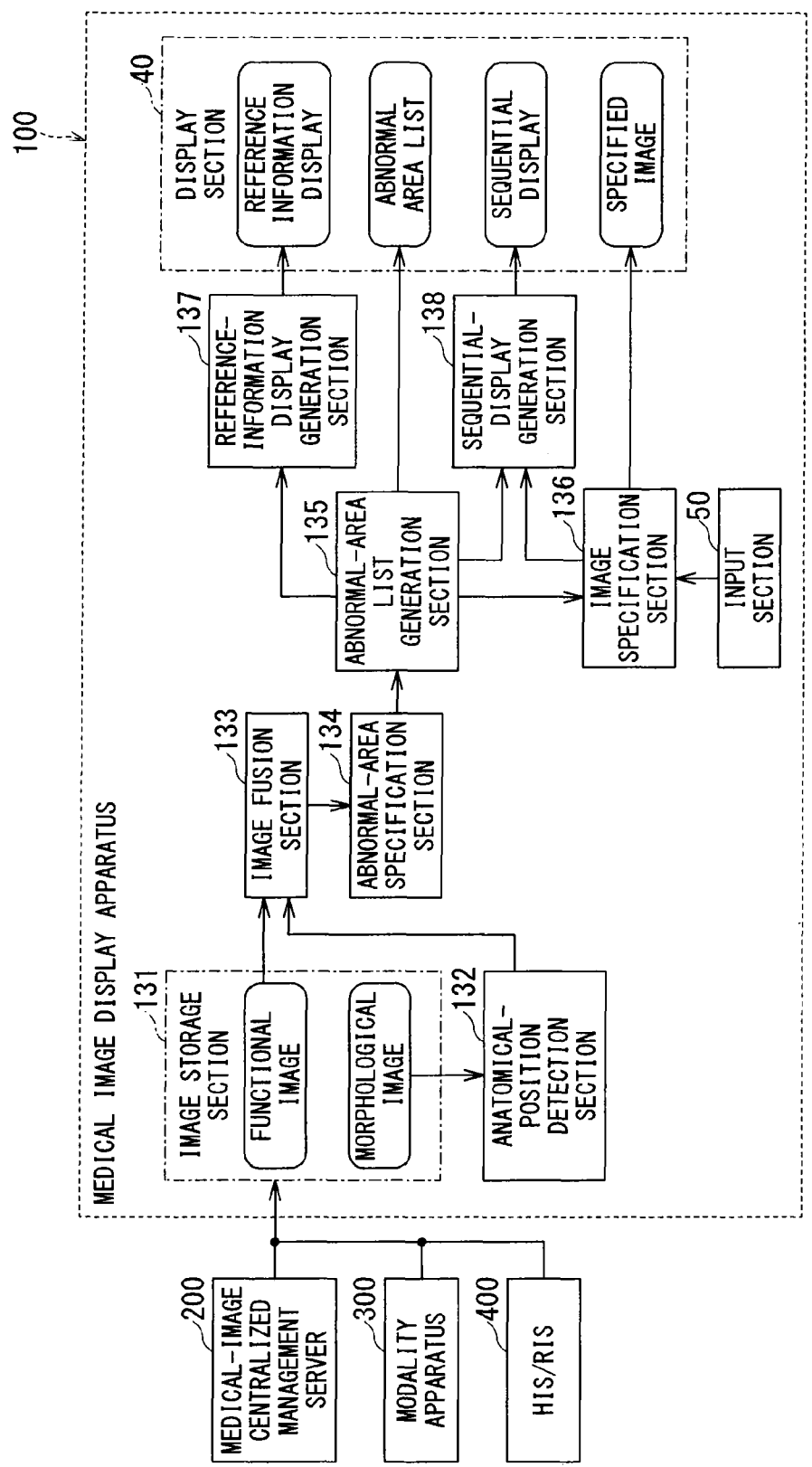
FIG. 2 is a functional block diagram to show a functional configuration example relating to a first embodiment of a medical image display apparatus relating to a first embodiment.

FIG. 2 is a functional block diagram to show a functional configuration example relating to a first embodiment of a medical image display apparatus 100 relating to a first embodiment. As shown in FIG. 2, the medical image display apparatus 100 includes an image storage section 131, an anatomical position detection section (position detection section) 132, an image fusion section 133, an abnormal-area specification section 134, an abnormal-area list generation section 135, an image specification section 136, a reference-information display generation section 137, a sequential-display generation section 138, a display section 40, and an input section 50. Among them, each function of the image storage section 131, the anatomical-position detection section 132, the image fusion section 133, the abnormal-area specification section 134, the abnormal-area list generation section 135, the image specification section 136, the reference-information display generation section 137, the sequential-display generation section 138 is realized by, for example, a processor (processing circuitry) of the main control section 30 executing a program stored in the storage section 20 (memory circuitry 20). It is noted that these functions may be realized by a plurality of processors cooperating together, or may be realized by a hardware logic such as a logic circuit without using a CPU.

Moreover, the display section 40 is made up of a function which is realized by a program stored in the storage section 20 being executed by the main control section 30, and a display function.

The image storage section 131 stores at least one functional image representing functional information of a tissue in an object, and at least one morphological image representing morphological information of the object. The functional image and morphological image to be stored by the image storage section 131 are configured to be stored in the image storage section 131 via a mobile storage medium or over a network.

A functional image is generated according to a value relating to an accumulation rate of a radioisotope (RI) which is selectively incorporated into an anatomical area where abnormality of the object is observed (abnormal area). The functional image refers to a nuclear medicine image acquired by a nuclear medicine diagnostic apparatus.

The morphological image includes morphological information of an anatomical area of an object. The morphological information is acquired by, for example, an X-ray CT apparatus or an MRI apparatus. It is noted that a nuclear medicine diagnostic apparatus such as a SPECT-CT apparatus can acquire a morphological image, while simultaneously collecting a functional image.

The anatomical-position detection section 132, which is configured to find a position of a characteristic structure of a human body by analyzing the morphological image, finds area information corresponding to a position of a region of interest of the functional image. The anatomical-position detection section 132 detects an anatomical position of the morphological image, and assigns information relating to the detected anatomical position (hereafter, referred to as "anatomical position information") to the morphological image data. As described later, the anatomical position information includes area information to which the anatomical position belongs (for example, an anatomical area such as the lung and the heart). It is noted that there is a case where the morphological image data is assigned with an anatomical position in advance. For example, assignment of an anatomical position to the morphological image data may be performed at the timing when an image is acquired at the modality apparatus 300, or at the timing when it is stored in the medical-image centralized management server 200. In that case, the detection processing of an anatomical position in the anatomical-position detection section 132 can be omitted. The method of detecting an anatomical position in the anatomical-position detection section 132 will be described later.

The anatomical position to be assigned to the morphological image data may be retained in a data format such as XML data and binary data in a state of being associated with corresponding morphological image data, etc. Moreover, the morphological image data to be acquired is data conforming to DICOM (Digital Imaging and Communication in Medicine) format, and the data of anatomical position may be retained as associated information in the DICOM standard.

The image fusion section 133 generates a fusion image in which a functional image and a morphological image where an anatomical position is detected are superimposed with each other. The generation method of a fusion image in the image fusion section 133 will be described later.

The abnormal-area specification section 134 specifies a region of interest based on a functional image. The region of interest means a region where abnormality is observed in the functional image. The abnormal-area specification section 134 specifies an anatomical area corresponding to a region of interest which is a region where abnormality is observed (abnormal area) from a fusion image based on an anatomical position of the fusion image. The specification method of an abnormal area in the abnormal-area specification section 134 will be described later.

The abnormal-area list generation section 135 generates an abnormal area list in which anatomical areas where abnormality is observed in the abnormal-area specification section 134 (abnormal areas) are listed based on anatomical positions of fusion image. The abnormal area list to be generated in the abnormal-area list generation section 135 will be described later.

The image specification section 136 specifies an image corresponding to an anatomical position selected from the abnormal area list, based on the anatomical position of fusion image. The image specification method of the image specification section 136 will be described later.

The sequential-display generation section 138 generates a sequential display image for displaying images specified in the image specification section 136 in the order of the anatomical positions listed in the abnormal area list. The sequential display image to be generated in the sequential-display generation section 138 will be described later.

The reference-information display generation section 137 generates a reference-information display item for displaying reference literatures, reference books, medical information, and case information relating to anatomical positions listed in the abnormal area list. The reference-information display item generated in the reference-information display generation section 137 will be described later.

(2) Action

Figure 3:
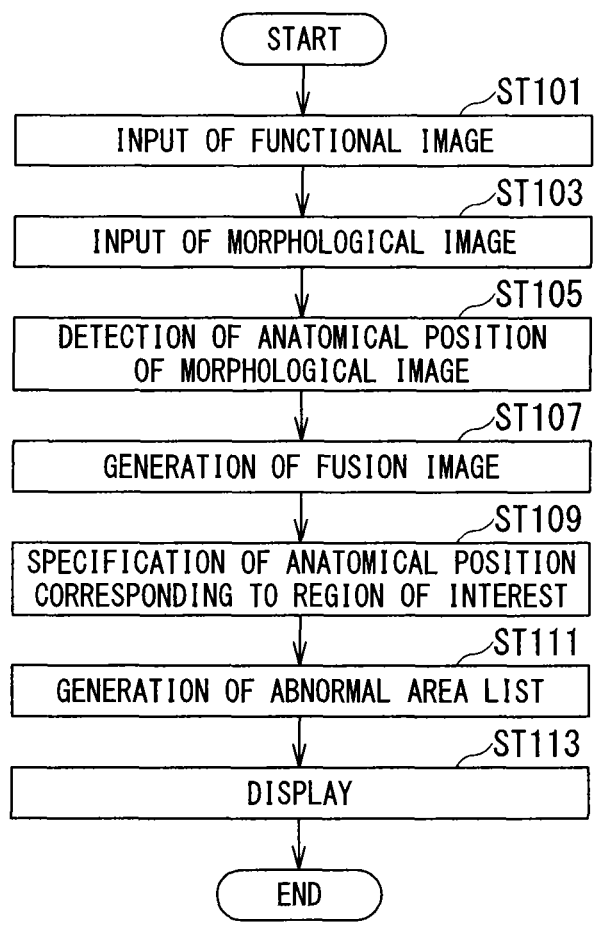
FIG. 3 is a flowchart to show an example of the action of the first embodiment of the medical image display apparatus relating to an embodiment.

FIG. 3 is a flowchart to show an example of the action of the first embodiment of the medical image display apparatus 100 relating to an embodiment.

In step ST101, a functional image is inputted to the image storage section 131.

In step ST103, a morphological image is inputted to the image storage section 131.

In step ST105, the anatomical-position detection section 132 detects an anatomical position from a morphological image stored in the image storage section 131.

Figure 4A:
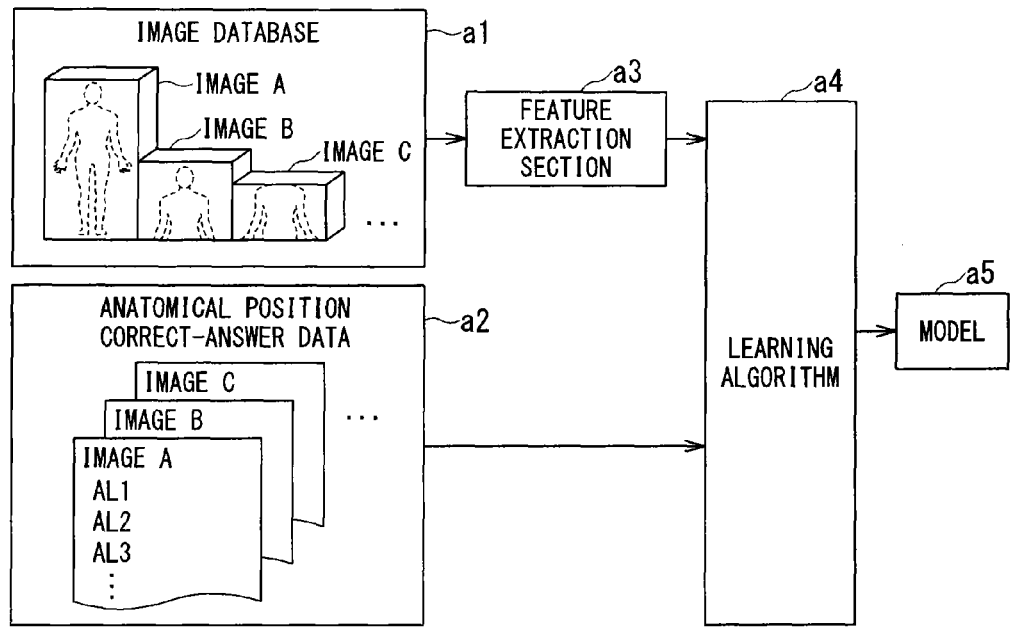
FIGS. 4A and 4B are diagrams to illustrate a detection method of anatomical positions.
Figure 4B:
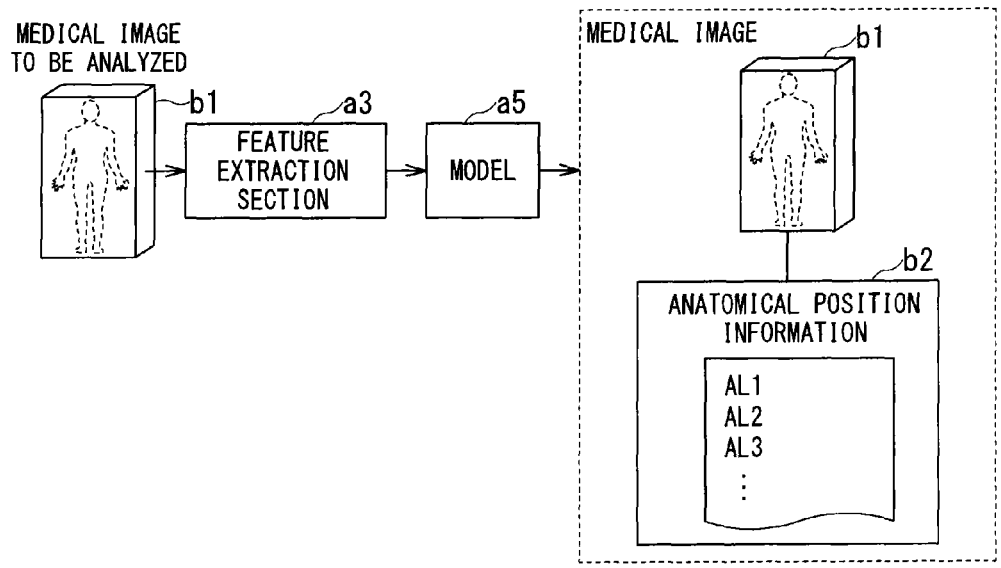

FIGS. 4A and 4B are diagrams to illustrate a detection method of anatomical positions. FIG. 4A shows an example of the generation method of a model a5 to be used for the detection of anatomical positions. The model a5 shown in FIG. 4A may be stored in advance in the storage section 20 of the medical image display apparatus 100, or may be stored in an external storage apparatus.

As shown in FIG. 4A, the model a5 to be used for the detection of anatomical positions is generated by a general machine learning or pattern recognition process. FIG. 4A shows an example in which the model a5 is generated by using image database a1 and anatomical position correct-answer data a2. The image database a1 refers to a collection of volume data acquired by an X-ray CT apparatus or an MRI apparatus on objects having different body shapes. As illustrated in FIG. 4A, the image database a1 includes not only volume data of whole body (image A), but also volume data of a part of body which is imaged (images B and C). The anatomical position correct-answer data a2 is data showing correct anatomical positions determined in advance by an expert such as a physician, on each image of the image database a1. As shown in FIG. 4A, a feature extraction section a3 extracts features from each volume data of the image database a1, and generates the model a5 by a learning algorithm a4 using the anatomical position correct-answer data a2. The model a5 is used for bringing the features extracted from the image database a1 into correspondence with anatomical positions. The model a5 includes, for example, a model by use of machine learning. Moreover, such a model may be one which is generated so as to vary depending on sexuality, ages, human races, and physical features etc., or may be one which can absorb such differences.

FIG. 4B shows an example of the processing to be executed in the anatomical-position detection section 132. The anatomical-position detection section 132 extracts features on image data b1 to be analyzed for which anatomical positions are unknown as with the feature extraction section a3 of FIG. 4A, and detects anatomical positions by using the model a5 which has been generated. To be more specific, it detects a local structure and calculates the position of the extracted local structure in the medical image as an anatomical position. Anatomical position information b2 calculated in this way is assigned to the image data b1 to be analyzed.

It is noted that the above described anatomical position can be detected by, without being limited to the above described method, a mathematical statistics framework called computational anatomy (a computational anatomy model).

FIGS. 5A to 5D are diagrams to explain kinds of local structures. The local structure is a characteristic structure of a human body which plays an important role to understand a medical image, and is sometimes called an anatomical landmark (AL). For example, FIG. 5A exemplifies local structures in a head and a neck. FIG. 5A exemplifies, in the order from the top, an anterior arch (tubercle) of atlas (cervical vertebra I), an superior tip of dens/peg (cervical vertebra II), a superior aspect of right eye globe, a superior aspect of left eye globe, a center of right eye globe, and a center of left eye globe. Similarly, FIG. 5B exemplifies, regarding local structures of a chest, a bifurcation of trachea, a apex of right lung, a apex of left lung, an inferior angle of right scapula, an inferior angle of left scapula, and a start of left subclavian artery (branching off aortic arch). FIG. 5C exemplifies, regarding local structures of an abdomen, a superior pole of right kidney, an superior pole of left kidney, a inferior pole of right kidney, an inferior pole of left kidney, a head of pancreas, and a tip of a tail of pancreas. FIG. 5D exemplifies, as local structures of a lower limb, a lateral epicondyle of right femur, a medial epicondyle of right femur, a lateral epicondyle of left femur, a medial epicondyle of left femur, a lateral condyle of right tibia, and a medial condyle of right tibia. Local structures are defined over the whole body in a granularity as shown in FIGS. 5A to 5D, and a plurality of local structures are determined for various bones, muscles, organs, and the like constituting a human body. Anatomical positions are detected for each of those local structures.

Such anatomical positions are retained as anatomical position information while being associated with medical image data. The anatomical position information may be retained as a database in the storage section 20, etc. in an XML or text format etc. while being associated with, for example, an ID for uniquely specifying a medical image, or may be retained integrally with the medical image data as associated information of DICOM.

The anatomical position information may include, in addition to information of anatomical positions, area information regarding such as the chest area and abdomen area to which local structures corresponding to the anatomical positions belong, and body system information according to functional schematics in a human body of the local structures corresponding to the anatomical positions.

Figures 6A, 6B:
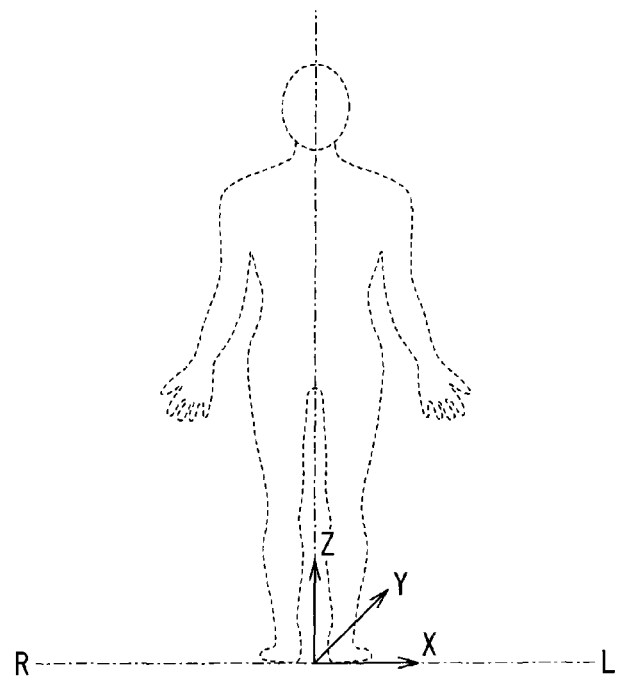
FIGS. 6A and 6B are diagrams to illustrate anatomical position information.

FIGS. 6A and 6B are diagrams to illustrate anatomical position information. The table of FIG. 6A shows an example of anatomical position information. The table of FIG. 6A showing anatomical position information shows, from the left, an identifier, a name, a reliability, a part, a body tissue, and a position in a patient coordinate system (X-axis, Y-axis, and A-axis) of an anatomical position. FIG. 6A exemplifies part of anatomical position information of the abdomen. The table of FIG. 6A shows, from the left, the identifier (ABDO25.C), the name (center of body of L5), reliability (0.87), the part (abdomen), the body tissue (skeletal system), and the patient coordinate system (X-axis (−3.1), Y-axis (23.4), Z-axis (90.0)). Similarly, a second row shows the identifier (ABDO32.C), the name (superior aspect of right iliac spine), reliability (0.82), the part (abdomen), the body tissue (skeletal system), and the patient coordinate system (X-axis (−11.1), Y-axis (−54.4), Z-axis (84.1)), and a third row shows the identifier (ABDO39.C), the name (superior aspect of left iliac spine), reliability (0.83), the part (abdomen), the body tissue (skeletal system), and the patient coordinate system (X-axis (−3.0), Y-axis (30.0), Z-axis (104.0)).

The identifier is an ID for uniquely specifying the anatomical position. The name shows a name of the local structure, and is shown by a technical term of anatomy and medicine. Reliability is a numerical value indicating accuracy of the anatomical position. Since an anatomical position is data estimated by calculation by means of a machine learning algorithm, pattern recognition, and the like, a numerical value indicating a level of accuracy at which the position is calculated is given for each anatomical position. In the example shown in FIG. 6A, reliability is represented by a numerical value in a range of 0 to 1, and a numeral value closer to 1 indicates higher reliability. The part shows an area of human body to which the local structure belongs, and is classified into, for example, a chest and an abdomen. The body tissue, which is classified according to the function of the local structure, is for example a nervous system, an skeletal system, and a respiratory system. Other than such Area and The body tissue, information regarding organ names such as the heart, lung, femur, etc. and units of anatomical structure may be included as the anatomical position information. The patient coordinate system shows an anatomical position by X-axis, Y-axis, and Z-axis coordinates.

FIG. 6B is a diagram to illustrate Patient's coordinate system. As shown in FIG. 6B, Patient's coordinate system is a coordinate system in which the left-and-right direction of patient is X-axis, the back-to-belly direction of patient is Y-axis, and the head-to-feet direction of patient is Z-axis. The X-axis increases with the center-to-right direction of patient being positive, the Y-axis increases with the center-to-back direction of patient being positive, and the Z-axis increases in the feet-to-head direction of patient. Such patient's coordinate system is represented in a relative fashion with respect to an arbitrary position such as a reference position included in the volume data.

It is noted that the example of FIGS. 6A and 6B shows an example of the information and data format included in the anatomical position information.

Next, description will be made referring back to the flowchart of FIG. 3.

In step ST107, the image fusion section 133 generates a fusion image in which a functional image and a morphological image in which anatomical positions are detected are superimposed with each other. While the functional image and the morphological image are acquired on the same object respectively, since they are acquired by different modality apparatuses, registration thereof is required at the time of superimposition. The fusion processing for fusing a functional image with a morphological image, which is performed in the image fusion section 133, is performed based on a common registration method which has been proposed, such as an MI (Mutual Information) method in which registration of images is performed at high accuracy by maximizing the amount of mutual information of two images, and a nonlinear fusion method.

Moreover, since gamma ray is attenuated in a living body, a functional image, which is a detection result of gamma ray, includes the effects of attenuation in a living body. A frequently used method for correcting such effect of attenuation in a living body is a method of generating an attenuation coefficient map showing a distribution of the attenuation coefficient of gamma ray energy of the nuclide to be used (hereafter referred to as an attenuation map), and correcting the detection result of gamma ray based on the attenuation map. According to this method, it is possible to correct the effect of the attenuation of gamma ray in a living body (hereafter, referred to as attenuation correction). This makes it possible to generate a nuclear medicine image at a higher accuracy compared with a case in which correction of attenuation is not performed. The image fusion section 133 synthesizes a highly accurate fusion image by the above-described attenuation correction when performing fusion processing for fusing a functional image with a morphological image.

Figure 7:
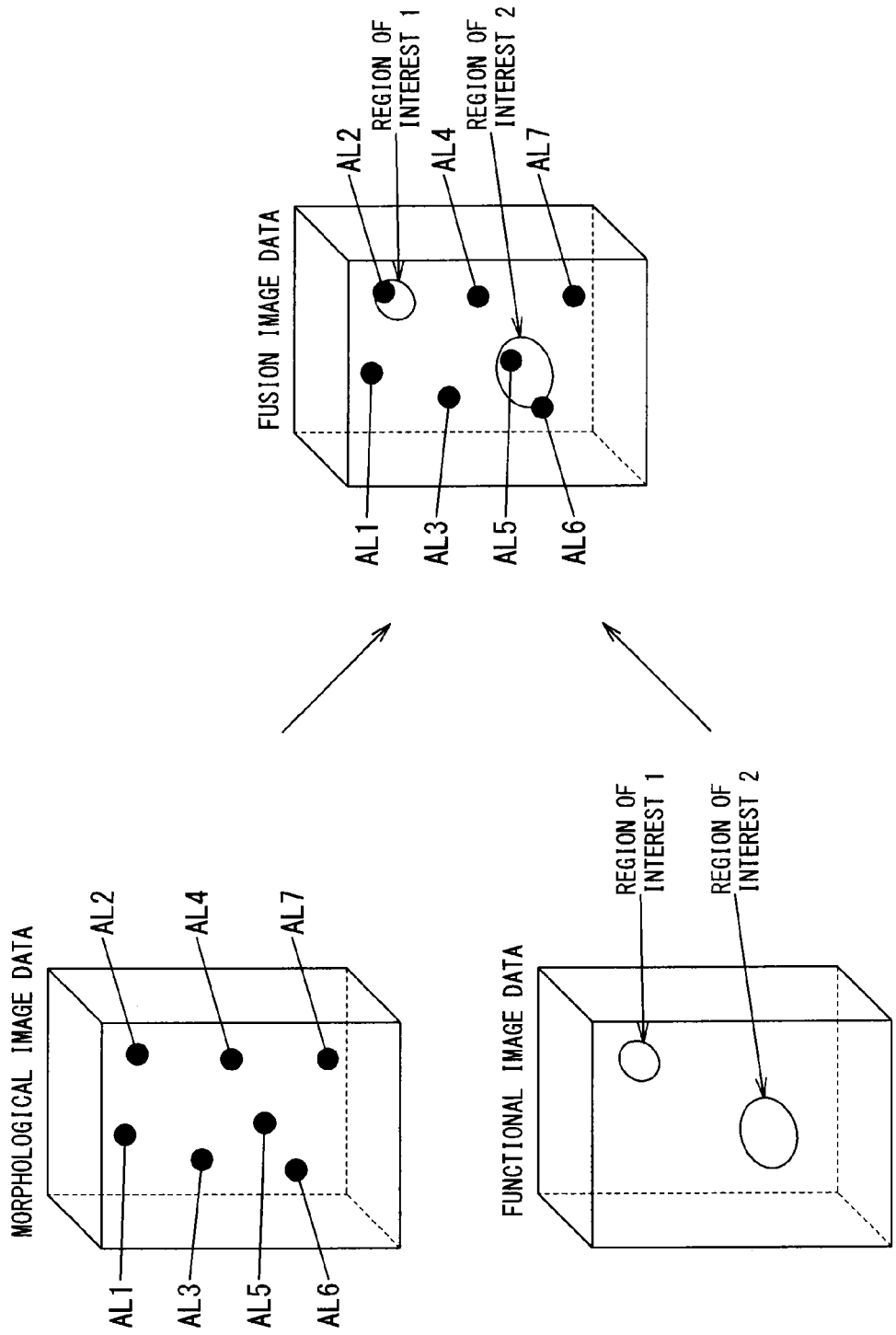
FIG. 7 is a diagram to illustrate a fusion image of the medical image display apparatus relating to an embodiment.

FIG. 7 is a diagram to illustrate a fusion image of the medical image display apparatus 100 relating to an embodiment. The volume data shown in the upper left of FIG. 7 shows an example of morphological image data, and the volume data shown in the lower left of FIG. 7 shows an example of functional image data. The volume data shown in the right side of FIG. 7 shows an example of fusion image data.

In the functional image data shown in the lower left of FIG. 7, regions of interest 1 and 2 are shown. A region of interest is, for example, a region where a functional abnormality is assumed. A nuclear medicine diagnostic apparatus acquires, as image data, data of dose distribution of gamma rays radiated from a radioactive medicine which is selectively incorporated into a living tissue of an object. The regions of interest 1 and 2 in the functional image data are regions where signals of gamma ray radiated from a portion where the radioactive medicine containing a radioisotope (RI) has accumulated are captured. In the functional image data, an accumulation of RI is observed in a portion where a tumor such as a cancer is present and a functional abnormality is observed. Moreover, by using a radioactive medicine containing an RI which is to be selectively incorporated in a particular organ and examining the level of accumulation of the RI in the particular organ, it is possible to diagnose the presence or absence of a functional abnormality of the organ. In this way, in the functional image, specification of the anatomical area of a place where a radioactive medicine containing a radioisotope (RI) has accumulated is the premise of imaging diagnosis.

It is noted that the functional image data is volume data, and the regions of interest 1 and 2 each show a region having a three-dimensional spatial expanse. An abnormal area is specified from an anatomical position included in a region of interest.

In the morphological image data shown in the upper left of FIG. 7, anatomical positions detected in the anatomical-position detection section 132 are shown. Shown in the upper left of FIG. 7 is an example in which anatomical positions AL1, AL2, AL3, AL4, AL5, AL6, and AL7 indicated by black circles are detected from the morphological image data.

Shown in the right side of FIG. 7 is an example of fusion image data in which the functional image data in the lower left of FIG. 7 and the morphological image data in the upper left of FIG. 7 are synthesized with each other. In the image fusion section 133, registration between the functional image and the morphological image, and attenuation correction are performed in the course of fusion processing. In the fusion image data synthesized in the image fusion section 133, the information of regions of interest detected in the functional image data is associated with the anatomical position information detected in the morphological image data. It is noted that even if the functional image and the morphological image are not actually superimposed with each other as shown in the right side of FIG. 7, it is sufficient if data in which the information of regions of interest detected in the functional image data and the anatomical position information detected in the morphological image data are associated with each other is generated.

As an example of the medical image display apparatus 100 relating to the present embodiment, description will be made on a method of specifying an abnormal area based on anatomical positions included in a region of interest by using fusion image data synthesized in the image fusion section 133.

The specification method of an abnormal area will be described referring back to the flowchart of FIG. 3.

In step ST109, the abnormal-area specification section 134 specifies an anatomical position corresponding to a region of interest from the fusion image.

In step ST111, the abnormal-area list generation section 135 generates an abnormal area list in which abnormal areas are listed. The abnormal area list is generated by searching anatomical position information of the anatomical positions included in the region of interest.

In step ST113, the abnormal area list is displayed on the display section 40.

Figure 8A:
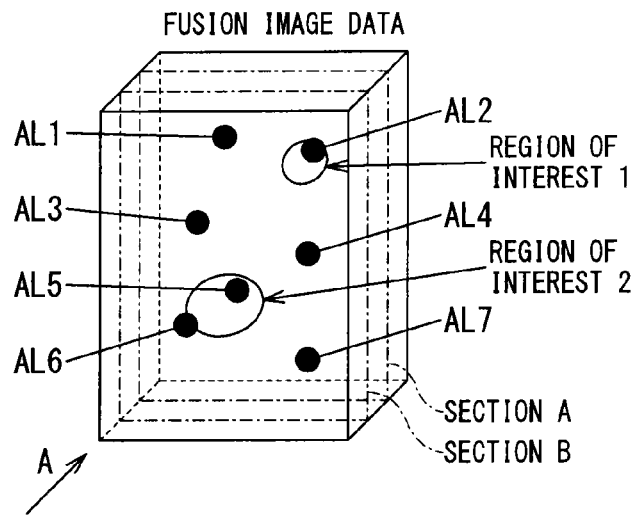
FIGS. 8A to 8C are diagrams to illustrate a method of specifying an anatomical position corresponding to a region of interest in the medical image display apparatus relating to an embodiment.
Figure 8B:
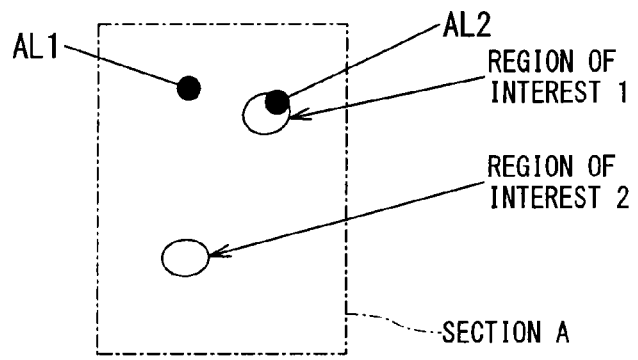
Figure 8C:
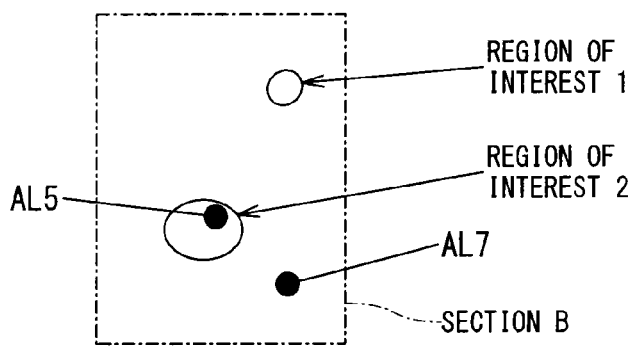

FIGS. 8A to 8C are diagrams to illustrate a method of specifying an anatomical position corresponding to a region of interest in the medical image display apparatus 100 relating to an embodiment. The abnormal-area specification section 134 specifies anatomical positions included in a region of interest of the fusion image.

In the example of FIG. 8A, a frame of one-dot chain line shows a section A and a section B of a fusion image shown in the right side of FIG. 7 when observed from a direction of the arrow A.

FIG. 8B shows an example of the section A shown in FIG. 8A. The section A of the fusion image data includes anatomical positions "AL1" and "AL2". Moreover, regions of interest 1 and 2 are shown in the section A. A region of interest has a three-dimensional shape having a spatial expanse, and a coronary section having a three-dimensional shape of the region of interest 1 is displayed in the section A of FIG. 8B. The section A of FIG. 8B shows an example in which the anatomical position "AL2" is included in the range of the region of interest 1.

FIG. 8C shows an example of the section B as in FIG. 8B. Anatomical positions "AL5" and "AL7" are included in the section B of the fusion image data. Moreover, regions of interest 1 and 2 are shown in the section B. The section B of FIG. 8C shows an example in which the anatomical position "AL5" is included in the range of the region of interest 2.

As shown in FIGS. 8A to 8C, anatomical positions of a fusion image are spatially distributed in the fusion image which is volume data. Therefore, an anatomical position included in a cut section of the fusion image varies depending on the position of cutting. Similarly, since the region of interest also has a three-dimensional shape in the fusion image data, its shape and area that appear on a section vary depending on the position of cutting. For example, when signals accumulated in a tumor etc. are collected, since the surface of the region of interest has a complex shape with irregularities, its shape that appears on a cut section varies depending on sections.

In FIGS. 8A and 8C, a method has been shown which specifies an anatomical position corresponding to a region of interest by acquiring a section in which an anatomical position exists and judging whether or not the anatomical position is included in the region of interest on the section. Whether or not the anatomical position is included in the region of interest can be specified by a general method from the coordinates of the region of interest and the coordinates of the anatomical position on the section. For example, by using a mathematical formula showing a profile of the region of interest, whether or not the coordinates of the anatomical position are included in the profile may be determined by an inequality, etc. Alternatively, by selecting some coordinates which are located at the end of the coordinate constituting the profile of the region of interest (for example, coordinates of apexes of a polygon, which imitates the shape of the region of interest) as representative coordinates, whether or not the anatomical position is included in the region of interest may be judged by comparing the representative coordinates with the coordinates of the anatomical position.

Moreover, it is possible to judge whether or not the anatomical position is included in the region of interest on the volume data. Each voxel position of a fusion image can be represented by a three-dimensional orthogonal coordinate system. Similarly, the coordinates of a voxel located in the vicinity of the anatomical position may be used as voxel coordinates showing the position of the anatomical position. The abnormal-area specification section 134 can specify anatomical positions included in a region of interest by judging, on the volume data, whether or not voxel coordinates showing the position of the anatomical position belong to a range of the voxels showing the region of interest.

By the above-described method, the abnormal-area specification section 134 specifies an anatomical position corresponding to a region of interest (hereafter, referred to as a functional abnormality position). The display section 40 may display the functional abnormality position specified in the abnormal-area specification section 134. Moreover, the abnormal-area list generation section 135 searches the anatomical position information, which is associated with the fusion image data, using the identifier or name of the functional abnormality position as a key, to generate an abnormal area list (ST111). The display section 40 displays the generated abnormal area list (ST113).

Figures 9, 10:
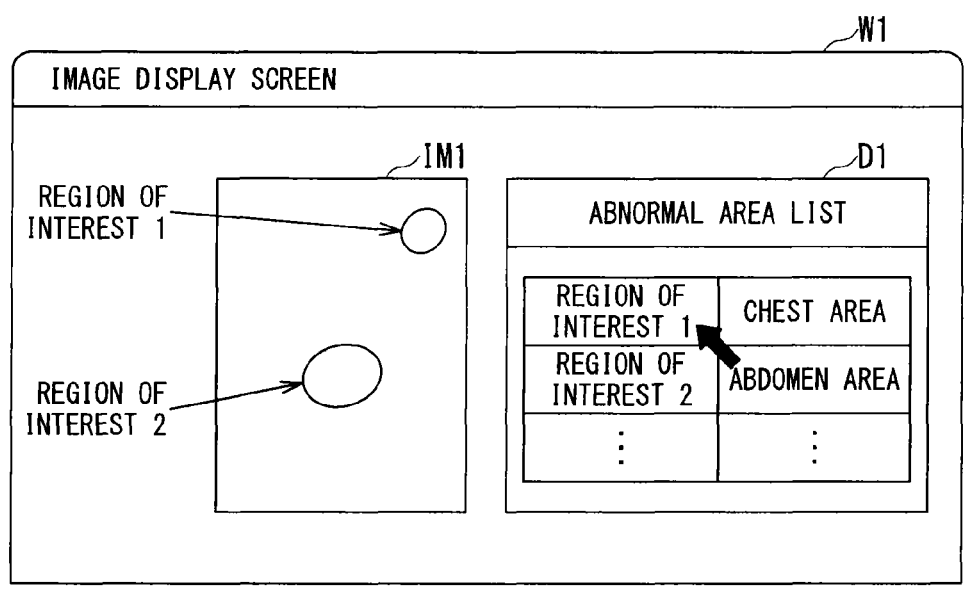
FIG. 9 is a diagram to illustrate an abnormal area list of the medical image display apparatus relating to an embodiment.
FIG. 10 is a diagram to illustrate a first display example of the medical image display apparatus relating to an embodiment.

FIG. 9 is a diagram to illustrate an abnormal area list of the medical image display apparatus 100 relating to an embodiment. FIG. 9 shows an example of the abnormal area list generated in the abnormal-area list generation section 135. The table of FIG. 9 shows, from the left, "Region of interest", "Functional abnormality position", "Part", "Body Tissue", and "Organ". The anatomical position information includes, as illustrated in FIG. 6, information such as "Part", "Body tissue", and "Organ" to which the anatomical position belongs, for each anatomical position. The abnormal-area list generation section 135 lists the results of searching the anatomical position information based on functional abnormality positions included in the region of interest, and generates an abnormal area list.

The first row of the table of FIG. 9 shows a result of searching the anatomical position information of a functional abnormality position "AL2" corresponding to an "Region of interest 1". It is seen from the anatomical position information that the functional abnormality position "AL2" belongs to the "Chest", also belongs to the body tissue of "Respiratory system", and is an anatomical position belonging to the organ of "Left lung". Similarly, the second row of the table of FIG. 9 shows results of searching the anatomical position information of an functional abnormality position "AL5" corresponding to an "Region of interest 2". It is shown that the functional abnormality position "AL5" belongs to the "Abdomen", also belongs to the body tissue of "Digestive system", and is an anatomical position belonging to the organ of "Liver".

In this way, the abnormal-area list generation section 135 generates an abnormal area list in which information of areas and organs to which functional abnormality positions belong are listed for each region of interest (ST111). The generated abnormal area list is displayed on the display section 40 (ST113). Hereafter, a display example of the abnormal area list to be displayed on the display section 40 will be described in FIGS. 10 to 12.

FIG. 10 is a diagram to illustrate a first display example of the medical image display apparatus 100 relating to an embodiment. FIG. 10 shows an example in which a fusion image IM1 is displayed on the left side of the image display screen W1, and an abnormal area list D1 is displayed on the right side thereof. In the fusion image IM1, regions of interest 1 and 2 are shown. Also, in the abnormal area list D1, "Chest area" is shown as the abnormal area corresponding to the region of interest 1, and "Abdomen area" as the abnormal area corresponding to the region of interest 2. As the abnormal area to be displayed in the abnormal area list D1, areas corresponding to regions of interest included in the fusion image displayed in the fusion image IM1 may be displayed, or abnormal areas specified in all the fusion images may be displayed in a list.

It is noted that in the example of the abnormal area list D1 of FIG. 10, although areas to which function abnormality positions belong are shown in a list, the subject to be listed thereon may be the name of local structure, or may be a body system or organ. Further, combinations thereof may be displayed.

The arrow shown in the abnormal area list D1 of FIG. 10 shows a cursor or pointer position, which is inputted from the input section 50 including a mouse etc. As shown by the arrow of FIG. 10, a user may select an area listed in the abnormal area list D1 via the input section 50 so that for example, the fusion image IM1 may be changed to a display corresponding to user's choice. For example, a frame may be displayed on a region of interest of the fusion image IM1 corresponding to a selected area, or the region of interest may be highlighted by being colored or shown by blinking light.

Moreover, a selected abnormal area or a coronal section of the fusion image including a functional abnormality position may be displayed on the fusion image IM1. The image specification section 136 specifies a corresponding coronal section image among the fusion image data, based on the anatomical position corresponding to selected information out of the display of the abnormal area list D1. Moreover, when a plurality of coronal section images are specified, all the coronal section images specified may be displayed. Moreover, the section including a selected abnormal area or a functional abnormality position may be an axial section, without being limited to a coronal section.

Figure 11:
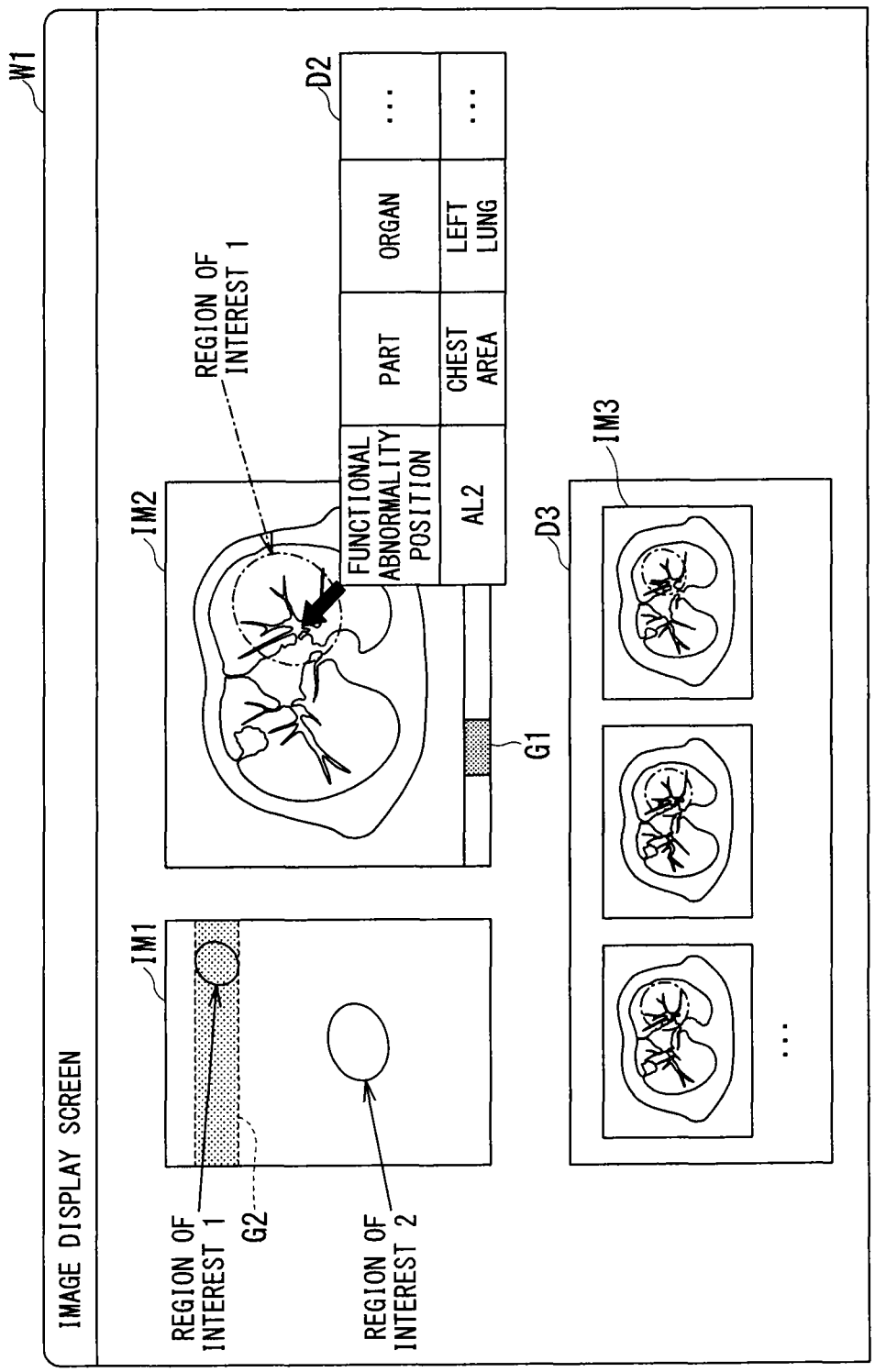
FIG. 11 is a diagram to illustrate a second display example of the medical image display apparatus relating to an embodiment.

FIG. 11 is a diagram to illustrate a second display example of the medical image display apparatus 100 relating to an embodiment. FIG. 11 shows an example in which after a user selects a region of interest 1 of the abnormal area list D1 of FIG. 10, an axial section image of the fusion image including the region of interest 1 is displayed.

In the upper left of FIG. 11, a fusion image IM1 is shown. A shaded region G2 in the fusion image IM1 shows a range of an axial section corresponding to the region of interest 1. In the upper right of FIG. 11, an axial section image IM2 of the fusion image corresponding to the region of interest 1 is shown. Below the axial section image IM2, a slider G1 is shown so that it is possible to continuously change the axial section image within a plurality thereof by operating the slider G1 to left or right. Moreover, in the lower part of FIG. 11, a thumbnail image list D3 is shown. In the thumbnail image list D3, thumbnail images IM3 of axial sections of the fusion image corresponding to the region of interest 1 are displayed in a list. Since a region of interest exists in a spatial fashion in the fusion image data, an axial section image including the region of interest 1 lies in a fixed range of the fusion image. Therefore, a plurality of thumbnail images IM3 are displayed on the thumbnail image list D3. Selected images of the thumbnail images IM3 displayed on the thumbnail image list D3 may be displayed on the axial section image IM2 in the upper right of FIG. 11.

Moreover, in the axial section image IM2 and each of the thumbnail images IM3, a frame, which is indicated by a frame of one-dot chain line, showing the region of interest 1 is shown. Superimposing a pointer or cursor on this frame via the input section 50 may result in a pop-up display of a table D2 corresponding to the region of interest 1 of the abnormal area list.

Although an example in which the image specification section 136 specifies a section for each region of interest in FIG. 11, the section may be specified for each part or organ.

Moreover, a sequential display image in which axial section images or coronal sections specified by the image specification section 136 are arranged in the order of anatomical positions listed in the abnormal area list may be displayed on the display section 40. Such a sequential display image in which specified sections are arranged in a sequence is generated in the sequential-display generation section 138. The sequential display image to be generated in the sequential-display generation section 138 may be one which sequentially displays regions of interest consisting of a plurality of section images for each region of interest or abnormal area, or one which sequentially displays section images including functional abnormality positions listed in the abnormal area list. Moreover, the sequential-display generation section 138 may generate an animation display (cine display) for continuously displaying images specified in the image specification section 136. Moreover, function abnormality positions included in each section may be displayed at corresponding position on the section, in conformance with the animation display.

Figure 12A:
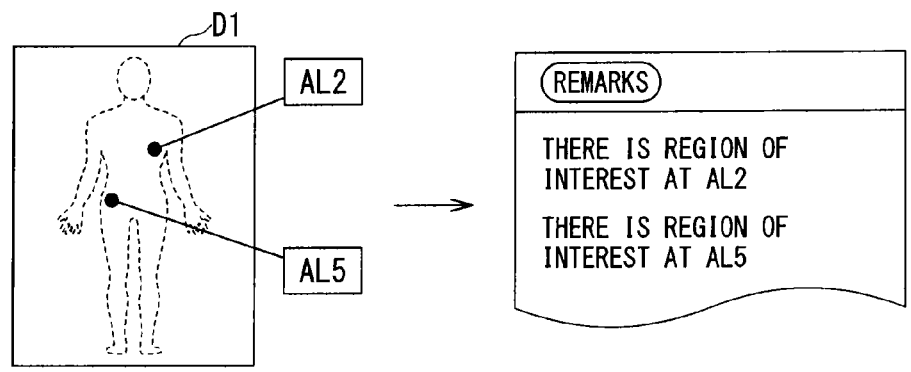
FIGS. 12A and 12B are diagrams to illustrate a third display example of the medical image display apparatus relating to an embodiment.
Figure 12B:
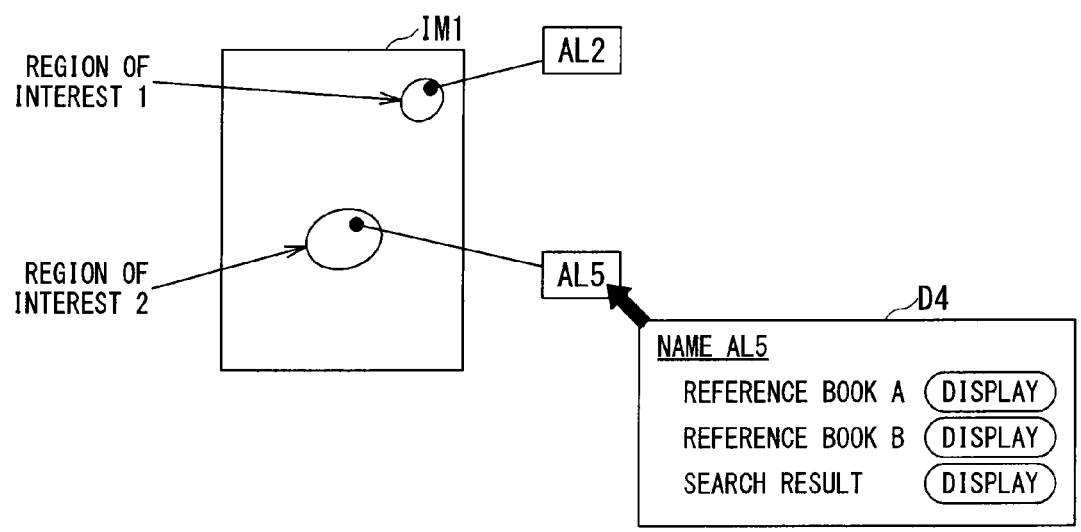

FIGS. 12A and 12B are diagrams to illustrate a third display example of the medical image display apparatus 100 relating to an embodiment.

In the left side of FIG. 12A, an example in which abnormal area list D1 is displayed using an anatomical chart of a human body is shown. An anatomical chart of a human body is intended for understanding the position, appearance, and shape of structures in a human body, and is represented by illustration or photograph etc. for each organ, area, and tract. In the example of FIG. 12A, "AL2" and "AL5" are displayed as the functional abnormality position at corresponding positions on an anatomical chart within a profile of anatomical chart showing the whole body of a human.

Moreover, in the right side of FIG. 12A, an example in which the contents of the abnormal area list D1 are automatically inserted as remarks of image-reading report is shown. FIG. 12A also shows an example in which based on the functional abnormality positions of the abnormal area list D1, sentences of "Region of interest exists at AL2" and "Region of interest exists at AL5" are automatically inserted as a content of the remarks. The content to be inserted into the remarks may be a sentence which is automatically generated by using a fixed form sentence and based on the contents of the abnormal area list, or a table generated in the abnormal-area list generation section 135 may be inserted as it is. Moreover, a content relating to a selected row in the abnormal area list D1 may be inserted into the remarks.

Moreover, an axial section image and a coronal section image including a functional abnormality position detected in the image specification section 136 may be presented to the user as a candidate of the key image when creating an image-reading report. When creating an image-reading report, there is a case where an image called a key image is appended. The key image refers to an image which is judged by an image-reading doctor to be the key to image reading among a plurality of images included in one piece of medial image data. Accordingly, as with the automatic insertion of remarks from the abnormal area list, an section image including a functional abnormality position listed in the abnormal area list D1 may be presented as a candidate for the key image to be appended to the image-reading report.

FIG. 12B shows an example of a reference-information display item generated in the reference-information display generation section 137. The reference-information display item is a display for providing a user with information of a local structure corresponding to a functional abnormality position. In the left side of FIG. 12B, a fusion image IM1 is shown. In the fusion image IM1, regions of interest 1 and 2, and functional abnormality positions "AL2" and "AL5" corresponding to each of them are shown. In the right side of FIG. 12B, a reference-information display item D4 is exemplified. As shown by the arrow in FIG. 12B, when the user superimposes a cursor or pointer on the functional abnormality position "AL5" through input from the input section 50, the reference-information display item D4 may be pop-up displayed. In the reference-information display item D4, the name of the functional abnormality position "AL5" and reference books A and B relating to AL5 are displayed. Further, a search result is displayed in which the result of searching on AL5 through the Internet etc. is displayed.

The configuration may be such that depressing a "Display" button in the reference-information display item D4 leads to a display of reference books relating to the anatomical position, thereby displaying cases relating to the anatomical position, or displaying an explanation of the relevant anatomical area from a dictionary of anatomy. Such reference books may be stored in the storage section 20 of the medical image display apparatus 100, or may be downloaded from an external storage apparatus, or the external storage apparatus may be directly referred to. Moreover, a search result of searching on the anatomical position through the Internet may be displayed. In this way, as a result of being able to survey about anatomical positions, users such as image-reading doctors can acquire various information from the medical image display apparatus 100.

Thus, the medical image display apparatus 100 relating to the present embodiment specifies abnormal areas based on anatomical positions corresponding to regions of interest (functional abnormality positions) of the fusion image, and thereby enables image-reading doctors etc. to easily acquire anatomical information on abnormal areas without relying on their own experience and knowledge. Moreover, since the medical image display apparatus 100 can display abnormal areas in a list, it is possible to prevent overlooking of abnormal areas, and further to easily create an image-reading report by taking advantage of the abnormal area list.

Second Embodiment

A second embodiment relates to a method which includes, in addition to performing the first embodiment, quantitatively analyzing an abnormal area, and comparing it with data acquired by a past examination.

(1) Configuration

Figure 13:
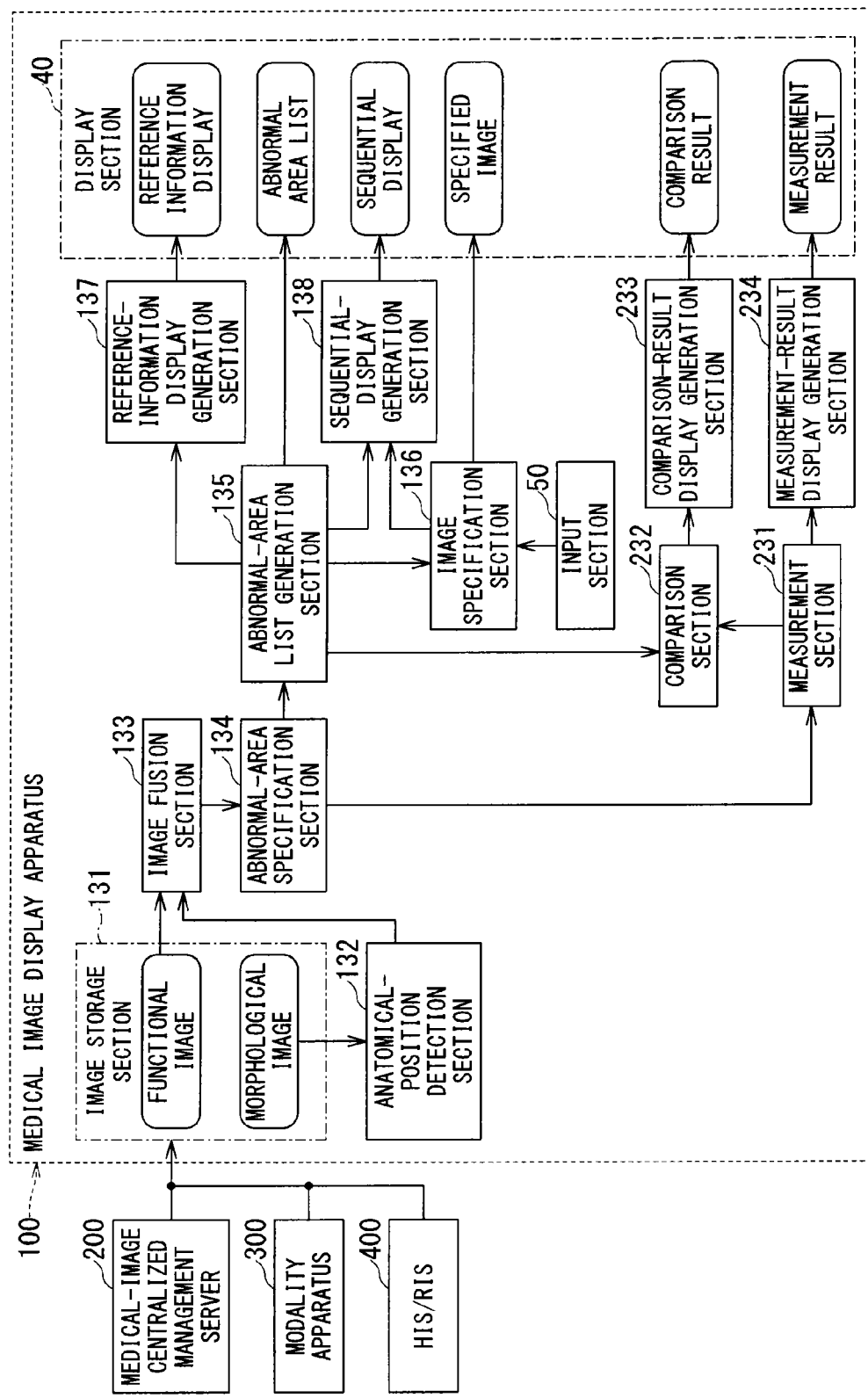
FIG. 13 is a functional block diagram to show a functional configuration example relating to a second embodiment of a medical image display apparatus relating to an embodiment.

FIG. 13 is a functional block diagram to show a functional configuration example relating to a second embodiment of a medical image display apparatus 100 relating to an embodiment. It is noted that the same configurations as those of the first embodiment are designated by the same reference numerals as shown in FIG. 2, thereby omitting description thereof.

As shown in FIG. 13, the medical image display apparatus 100 includes in addition to the configuration of the first embodiment, a measurement section 231, a comparison section 232, a comparison-result display generation section 233, and a measurement-result display generation section 234. Each function of the measurement section 231, the comparison section 232, the comparison-result display generation section 233, and the measurement-result display generation section 234 is one realized by, for example, a main control section 30 executing a program stored in a storage section 20.

The measurement section 231 measures an area or volume of a region where abnormality is observed (region of interest) of abnormal area based on a functional abnormality position. The measurement method of the size of a region of interest in the measurement section 231 will be described later.

The comparison section 232 compares the abnormal area list of a fusion image acquired in the past on an object with the abnormal area list of a latest fusion image to calculate a comparison result. Moreover, it also compares a value measured on a fusion image acquired in the past in the measurement section with a value measured on a latest fusion image in the measurement section. The comparison method of the comparison section 232 will be described later.

The measurement-result display generation section 234 generates a measurement-result display for each functional abnormality position of an abnormal area from a value measured in the measurement section 231. The measurement-result display generated in the measurement-result display generation section 234 will be described later.

The comparison-result display generation section 233 generates comparison-result display information from a comparison result of the comparison section 232. The comparison-result display information to be generated in the comparison-result display generation section 233 will be described later.

(2) Action

Figure 14:
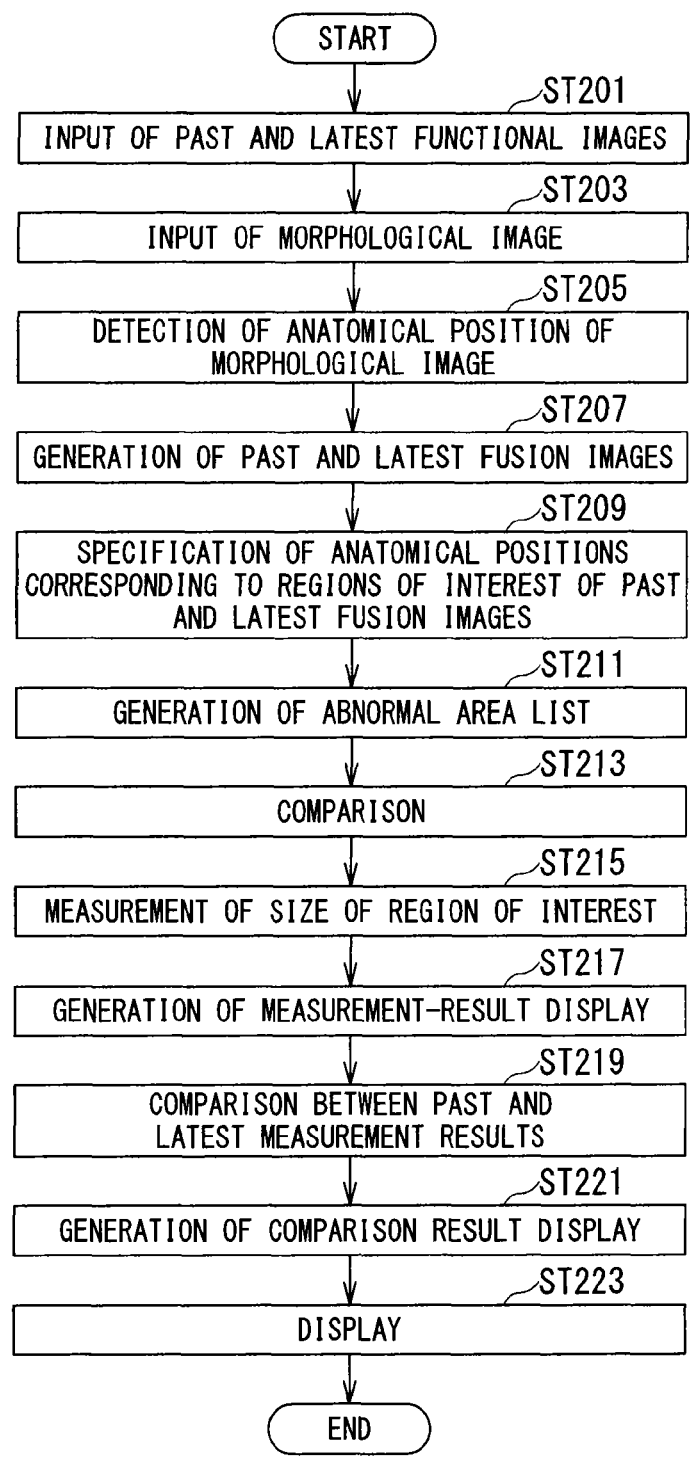
FIG. 14 is a flowchart to show an example of the action of the second embodiment of the medical image display apparatus relating to an embodiment.

FIG. 14 is a flowchart to show an example of the action of the second embodiment of the medical image display apparatus 100 relating to an embodiment. In FIG. 14, the action will be described by taking an example of a case where latest examination data and past examination data, which are acquired on an object, are compared.

In step ST201, functional images acquired at past and latest examinations are inputted respectively to the image storage section 131.

In step ST203, a morphological image acquired at a past examination is inputted to the image storage section 131. It is noted that when a morphological image is acquired again at a latest examination, a morphological image acquired at the latest examination is inputted to the image storage section 131.

In step ST205, the anatomical-position detection section 132 detects an anatomical position on the morphological image. It is noted that when anatomical position information is already associated with the morphological image, the processing may be omitted.

In step ST207, the image fusion section 133 synthesizes functional images acquired at past and latest examinations respectively with a past morphological image, and generates a past fusion image and a latest fusion image, respectively. It is noted that when a morphological image is acquired at the latest examination, the latest functional image may be synthesized with the latest morphological image, or the past and latest functional images may be respectively synthesized with a latest morphological image.

In step ST209, the abnormal-area specification section 134 specifies an abnormal area from the past and latest fusion images. The abnormal area is specified based on the anatomical position included in the region of interest as in the method described in the first embodiment.

In step ST211, the abnormal-area list generation section 135 generates a display in which abnormal areas are listed.

In step ST213, the comparison section 232 compares abnormal area lists generated on past and latest fusion image data. Regions of interest shown in the abnormal area list generated in the abnormal-area list generation section 135 can be identified by the functional abnormality position included therein. That is, the regions of interest of past and latest fusion images can be brought into correspondence to each other at functional abnormality positions included in the regions of interest, respectively.

Figure 15:
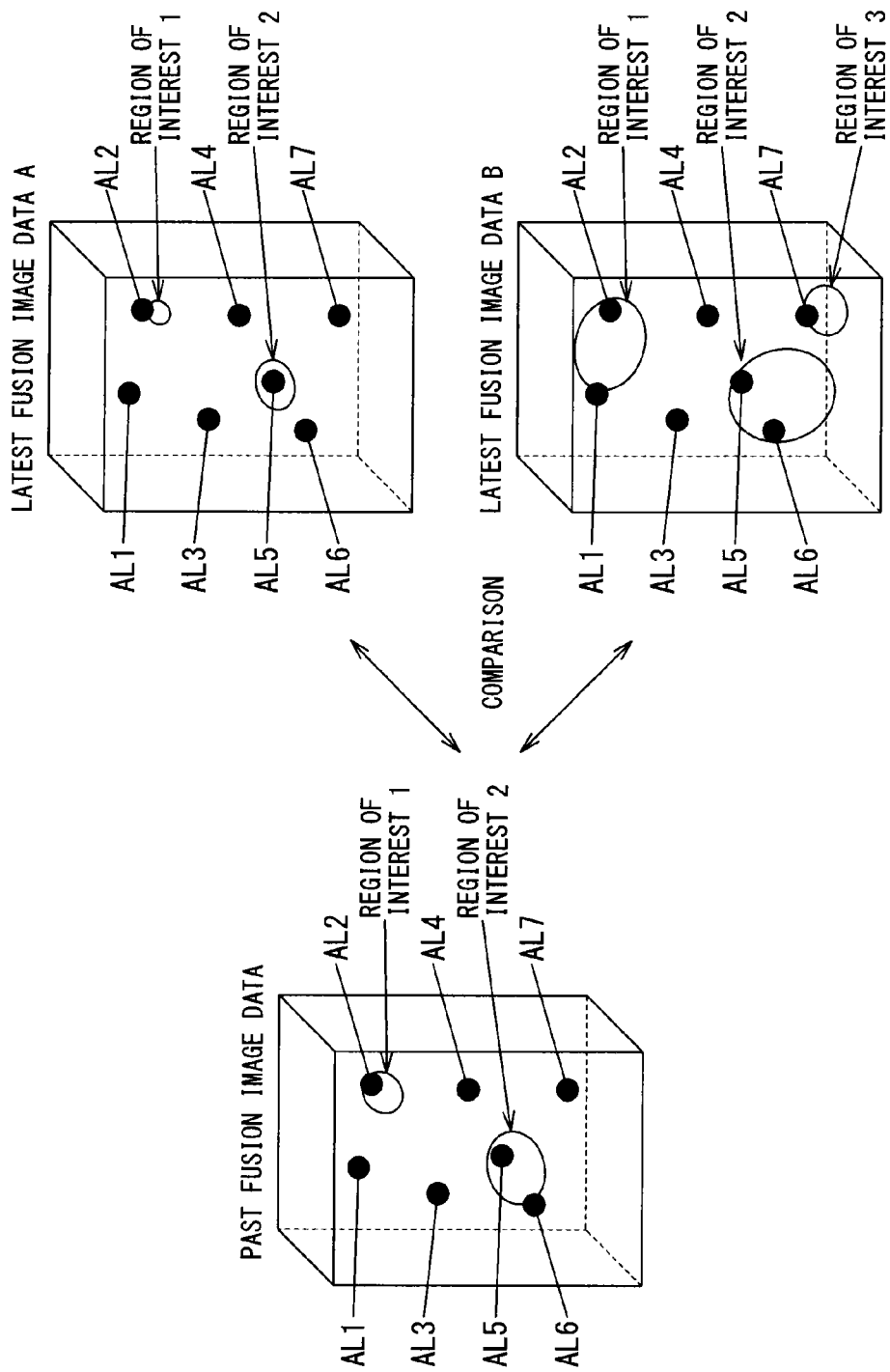
FIG. 15 is a diagram to illustrate past and latest fusion images of the medical image display apparatus relating to an embodiment.

FIG. 15 is a diagram to illustrate past and latest fusion images of the medical image display apparatus 100 relating to an embodiment. In the left side of FIG. 15, past fusion image data is shown. Moreover, in the right side of FIG. 15, two examples are shown as the latest fusion image data. Latest fusion image data A (the upper right in FIG. 15) shows an example in which the latest fusion image data A indicates a recovery trend compared to in the past, and latest fusion image data B (the lower right in FIG. 15) shows an example in which it indicates a deteriorating trend compared to in the past.

In the past fusion image data, the latest fusion image data A, and the latest fusion image data B shown in FIG. 15, as in the fusion image data shown in the right side in FIG. 7, regions of interest 1 and 2, anatomical positions "AL1, AL2, AL3, AL4, AL5, AL6, and AL7" are shown respectively. In the example of the latest fusion image data A, which indicates a recovering trend compared to in the past, the ranges of the regions of interest 1 and 2 have decreased compared to in the past fusion image. On the other hand, in the example of the latest fusion image data B, in which it indicates a deteriorating trend compared to in the past, the ranges of the regions of interest 1 and 2 have increased compared to in the past fusion image. In addition, a region of interest 3 is newly shown.

It is noted that regions of interest of a past fusion image and a latest fusion image can be brought into correspondence with each other from functional abnormality positions included in the regions of interest of the latest fusion image, and functional abnormality positions included in the regions of interest of the past fusion image. For example, in the past fusion image data of FIG. 15, the region of interest 1 includes "AL2" as the functional abnormality position. In the latest fusion image data A in the upper right of FIG. 15, it is judged that the region of interest which includes "AL2" as the functional abnormality position corresponds to the region of interest 1. Similarly, in the latest image data B in the lower right of FIG. 15, it is judged that the region of interest which includes "AL2" as the functional abnormality position corresponds to the region of interest 1.

The abnormal-area specification section 134 specifies anatomical positions included in regions of interest for each of the past and latest fusion images exemplified in FIG. 15 (ST209). An abnormal-area list display is generated on each of the past and latest fusion images from specified anatomical positions, by the abnormal-area list generation section 135 (ST211).

FIGS. 16A to 16C are diagrams to illustrate abnormal area lists of past and latest fusion images of the medical image display apparatus 100 relating to an embodiment.

FIG. 16A shows an example of an abnormal area list of past fusion image data. In an example of the past fusion image shown in the left side of FIG. 15, regions of interest 1 and 2 are shown. FIG. 16A shows that "AL2" is specified as the functional abnormality position included in "Region of interest 1", and that as a result of searching anatomical position information of past fusion images, the area to which "AL2" belongs is "Chest", the body tissue is "Respiratory system", and the organ is "Left lung". Similarly, in FIG. 16A, "AL5" and "AL6" are specified as the functional abnormality position included in "Region of interest 2". And "Abdomen" is shown as the area to which "AL5" and "AL6" belong, and "Digestive system" as the body tissue, and "Liver" as the organ.

FIG. 16B shows an example of the abnormal area list of the latest fusion image data A. In the example shown in the upper right of FIG. 15, as in the past fusion image data, the regions of interest 1 and 2 are shown. In FIG. 16B, differing from in FIG. 16A, the functional abnormality position corresponding to the region of interest 2 is "AL5" alone.

FIG. 16C shows an example of the abnormal area list of the latest fusion image data B. In the example in the lower right of FIG. 15, in addition to the regions of interest 1 and 2, a region of interest 3 is shown. In FIG. 16C, differing from in FIG. 16A, "AL2" in addition to "AL1" is specified as the functional abnormality position corresponding to the region of interest 1. Moreover, in the second row of the abnormal area list shown in FIG. 16C, "Chest" is shown as the part to which "AL2" belongs, "Respiratory system" as the body tissue, and "Right lung" as the organ. Further, the abnormal area list shown in FIG. 16C shows a region of interest 3 which is different from in FIG. 16A. "AL7" is specified as the functional abnormality position corresponding to the region of interest 3, and "Abdomen" is shown as the area to which "AL7" belongs, "Urinary system" as the body tissue, and "Left kidney" as the organ.

The comparison section 232 may compare past and latest fusion image data in the type or number of the functional abnormality position corresponding to the region of interest. For example, in the latest fusion image data A shown in FIG. 16B, the number of the functional abnormality positions corresponding to the region of interest 2 has decreased. The comparison section 232 may judge that the latest fusion image data A indicates a "recovering trend" since the number of the functional abnormality position corresponding to the region of interest 2 has decreased. On the other hand, in the latest fusion image data B shown in FIG. 16C, the functional abnormality position "AL1" included in the region of interest 1 is added. In addition, a region of interest 3 has newly occurred. From what has been described so far, the comparison section 232 may judge that the latest fusion image data B indicates a "deteriorating trend".

In FIGS. 16A to 16C, while a method in which the comparison section 232 compares past and latest examination data based on the abnormal area list has been described, the comparison section 232 may compare the past and latest examination data based on a measurement result in the measurement section 231 which measures the size of the region of interest.

Referring back to the flowchart of FIG. 14, comparison based on a measurement result in the measurement section 231 will be described.

In step S215, the measurement section 231 measure the size of the region of interest. The size of the region of interest of abnormal area in the measurement section 231 may be the area of the region of interest of the section image in which a functional abnormality position is present, or a surface area or volume of a three-dimensional region of interest measured based on voxel coordinates etc. of the region of interest. Moreover, since the amount or concentration of accumulated radiation can be obtained as a numerical value from a functional image data, a value relating to the accumulation rate of such RI contained in a voxel included in a region of interest (hereafter, referred to as a "RI accumulation value") may be calculated as the size of the region of interest. Furthermore, a distance from the functional abnormality position included in a region of interest to the profile of the region of interest may be measured as the size of the region of interest. Further, for example, a proportion of the size of a region of interest to the size of an abnormal area may be measured.

In step ST217, the measurement-result display generation section 234 generates a measurement-result display based on the measurement result.

In step ST219, the comparison section 232 compares measurement results of past and latest examination data.

In step ST221, the comparison-result display generation section 233 generates comparison-result display information based on the comparison result.

In step ST223, the measurement-result display information and the comparison-result display information are displayed on the display section 40, respectively.

FIGS. 17A to 17C are diagrams to illustrate a first measurement result of past and latest fusion images of the medical image display apparatus 100 relating to an embodiment. FIGS. 17A to 17C exemplify a result that the measurement section 231 has measured the volume of a region of interest. For example, it is possible to calculate the volume of a region of interest from the number of voxels included in the region of interest.

FIG. 17A shows volumes measured on regions of interest of past fusion image data. The column of Volume in the first row of FIG. 17A shows "15 mm$^3$ (cubic millimeter)" as the volume of region of interest 1. Similarly, the column of Volume in the second row of FIG. 17A shows "30 mm$^3$" as the volume of region of interest 2.

FIG. 17B shows volumes measured on regions of interest of latest fusion image data A. The column of Volume in the first row of FIG. 17B shows "8 mm$^3$ (cubic millimeter)" as the volume of region of interest 1. Similarly, the column of Volume in the second row of FIG. 17B shows "20 mm$^3$" as the volume of region of interest 2.

FIG. 17C shows volumes measured on regions of interest of latest fusion image data B. The column of Volume in the first row of FIG. 17C shows "60 mm$^3$ (cubic millimeter)" as the volume of region of interest 1. Similarly, the column of Volume in the second row of FIG. 17C shows "90 mm$^3$" as the volume of region of interest 2, and the column of Volume in the third row shows "15 mm$^3$" as the volume of region of interest 3.

The comparison section 232 can quantitatively judge whether latest fusion image data indicates a recovering trend or a deteriorating trend, by comparing the volumes of the regions of interest 1 and 2 of the past fusion image data shown in FIG. 17A with the volumes of the regions of interest 1 and 2 of the latest fusion image data.

FIGS. 18A and 18B are diagrams to illustrate a comparison result based on a first measurement result of past and latest fusion images of the medical image display apparatus 100 relating to an embodiment. "Volume increase/decrease (%)" shown in FIGS. 18A and 18B shows a value of a latest volume divided by a past volume as an example of a numerical value to show increase/decrease of the volume of region of interest. The case where there is no increase/decrease in volume is represent by 100%, and the numerical value becomes less than 100% when the volume decreases, and more than 100% when the volume increases.

FIG. 18A shows a result of comparison between past fusion image data and latest fusion image data A. The volume increase/decrease of the region of interest 1 shown in the first row of FIG. 18A shows "53%". Similarly the volume increase/decrease of region of interest 2 shown in the second row show "67%". It is seen from the comparison result of the volumes of regions of interest of the past and latest fusion images that the number of regions of interest of the latest fusion image data A has decreased compared to in the past.

FIG. 18B shows a result of comparison between past fusion image data and latest fusion image data B. The volume increase/decrease of region of interest 1 shown in the first row of FIG. 18B show "400%". Similarly, the volume increase/decrease shown in the second row shows "300%". It is seen from the comparison result of the volumes of regions of interest of the past and latest fusion images that the volumes of the regions of interest have increased compared to in the past in the latest fusion image data B. It is noted that as for the region of interest 3 for which no volume data exists in the past fusion image data, a symbol "-" is shown since comparison of volume cannot be performed. Moreover, since it is a newly detected region of interest, instead of "-", a display meaning a new region of interest (for example, "Novel") may be displayed as the comparison result.

Although a case in which the increase/decrease of volume is compared in percentage has been shown in the examples of FIGS. 18A and 18B, an increase/decrease value of volume may simply be a result that a past volume is subtracted from a latest volume.

Moreover, although the volume of region of interest has been described as an example of the reference for comparison in the comparison section 232, it may be the surface area of region of interest, and the area of region of interest in a section mage in which a functional abnormality position exists. Moreover, the measurement section 231 can also calculate an integrated result of RI accumulation values corresponding to voxels included in a region of interest. The comparison section 232 may perform comparison between past and latest fusion image data according to such RI accumulation value.

FIGS. 19A to 19C are diagrams to illustrate a second measurement result and comparison result between past and latest fusion images of the medical image display apparatus 100 relating to an embodiment. FIG. 19 shows an example of comparison result in the comparison section 232 based on an integrated value of RI accumulation values corresponding to voxels included in a region of interest, and calculated in the measurement section 321.

FIG. 19A shows an example of measurement result of past fusion image data. As the measurement result, integrated values of RI accumulation value of regions of interest 1 and 2 are shown. The first row of FIG. 19A shows "25" as the RI accumulation value of the region of interest 1. Similarly, the second row shows "15" as the RI accumulation value of the region of interest 2.

FIG. 19B shows a result of comparison between a measurement result of latest fusion image data A and a measurement result of past fusion image data. The first row of FIG. 19B shows "10" as the RI accumulation value of the region of interest 1. Moreover, increase/decrease (%) of RI accumulation value is shown as the result of comparison with past fusion image data. The increase/decrease (%) of RI accumulation value shows a value of a latest RI accumulation value divided by a past RI accumulation value in percentage as with the increase/decrease of volume described in FIGS. 18A and 18B. The RI accumulation value is represented by 100% when there is no increase/decrease, a numerical value less than 100% when the RI accumulation value decreases, and a numerical value more than 100% when the RI accumulation value increases. The increase/decrease of the RI accumulation value of the first row is "40%". Similarly, the second row shows "15" as the RI accumulation value of the region of interest 2, and the increase/decrease of RI accumulation value shows "100%" indicating that there is no increase/decrease compared to in the past fusion image data.

FIG. 19C shows a result of comparison between past fusion image data and latest fusion image data B. As with FIG. 19B, the first row shows "35" as the RI accumulation value of region of interest 1, and the increase/decrease (%) of RI accumulation value, which is a result of comparison with past fusion image data, is "140%". Similarly, the second row shows "25" as the RI accumulation value of the region of interest 2, and "167%" as the increase/decrease (%) of RI accumulation value, which is the result of comparison with past fusion image data. Further, although the third row shows "20" as the RI accumulation value of region of interest 3, since the region of interest 3 has not been specified in the past fusion image data, "-" is shown for the increase/decrease (%) of RI accumulation value, which is a comparison result.

In the example of FIGS. 19A to 19C, a case in which the comparison section 232 performs comparison between past and latest fusion image data based on the integrated value of RI accumulation values of each region of interest, which is measured in the measurement section 231. Performing comparison between past and latest fusion image data according to such RI accumulation value makes it possible to quantitatively compare past and latest images as in the case of comparison by volume.

Moreover, the comparison section 232 can also perform comparison by combining comparison by volume and comparison of RI accumulation value. For example, in the example of FIG. 18A, the volume increase/decrease of the region of interest 2 of the latest fusion image data A has decreased to "67%". On the other hand, in the example of FIG. 19B, the increase/decrease of RI accumulation value of the latest fusion image data A shows "100%", indicating that there is no increase/decrease. Based on these two numerical values, the comparison section 232 will obtain a comparison result that while the volume of abnormal area has decreased, the RI accumulation value has not changed. In such a case, it can be judged that for example, abnormal cells and tissues which have occurred in an abnormal area have increased more than in a past examination result, and therefore the abnormal area is comprehensively on a deteriorating trend.

Further, the comparison section 232 can compare ranges of region of interest respectively specified in a past fusion image and a latest fusion image. For example, it is possible to calculate a ratio or proportion at which voxel coordinates of a voxel included in each region of interest are the same. Calculating a ratio or proportion at which voxel coordinates of a voxel included in each region of interest are the same makes it possible to quantitatively calculate a portion which has newly increased or decreased from the past.

Moreover, it is possible to calculate a ratio of region of interest in which a functional abnormality position is included with respect to the size of an organ to which the functional abnormality position belongs. The size of an organ may be measured from a morphological image by a general measurement method, or may be calculated based on a size of the organ predicted from patient's physical features included in the patient information.

Further, it is possible to measure the size of a region of interest from a functional abnormity position and coordinates of an anatomical position located in the vicinity thereof, and also to measure a distance from a functional abnormity position to a particular position of the region of interest.

Based on the values measured in this way, the measurement-result display generation section 234 generates measurement-result display information. Moreover, the comparison section 232 performs comparison between past and latest examination data based on measured values, and the comparison-result display generation section 233 generates comparison-result display information according to the comparison result. The generated measurement-result display information or comparison-result display information is displayed on the display section 40.

Moreover, the measurement-result display generation section 234 and the comparison-result display generation section 233 may generate information to be inputted to the remarks without being limited to display images to be displayed on the display section 40 from information generated by the measurement section 231 and the comparison section 232. For example, wordings corresponding to the table showing measurement results and the results determined in the comparison section 232 may be automatically inserted into the remarks.

Figure 20A:
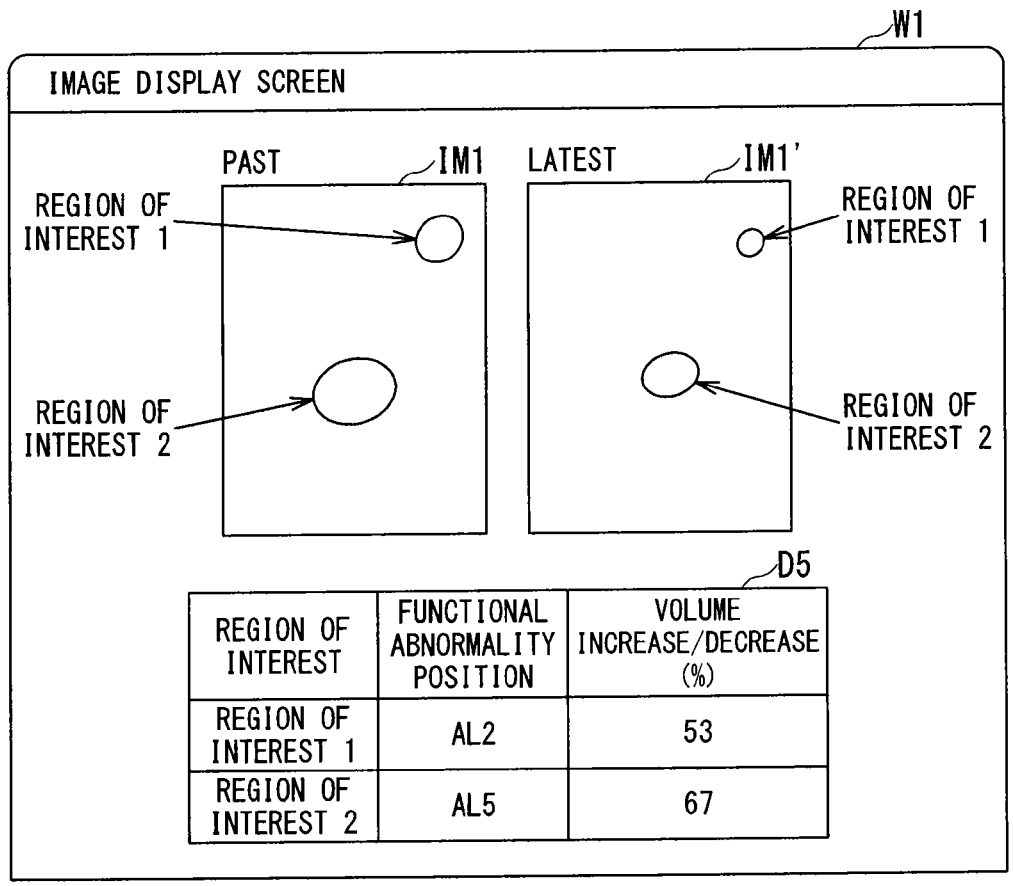
FIGS. 20A and 20B are diagrams to illustrate a display example of a comparison result between past and latest fusion images of the medical image display apparatus relating to an embodiment.
Figure 20B:
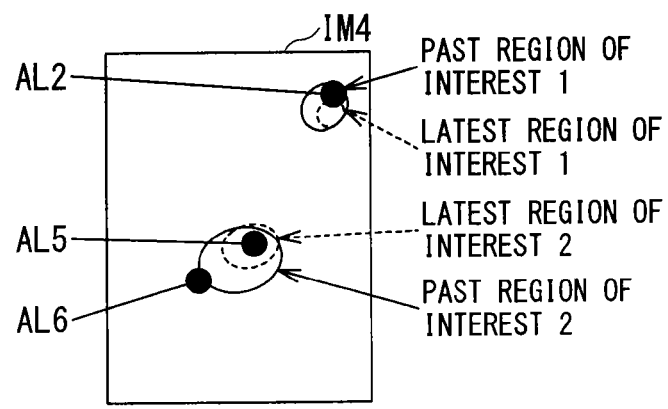

FIGS. 20A and 20B are diagrams to illustrate a display example of a comparison result between past and latest fusion images of the medical image display apparatus 100 relating to an embodiment. FIGS. 20A and 20B show a display example of a comparison result in which past fusion image data is compared with latest fusion image data A.

FIG. 20A shows an example in which a past fusion image IM1 is displayed in the upper left of the image display screen W1, and a latest fusion image IM1' in the upper right thereof, side by side. In the lower portion of FIG. 20A, a comparison result display D5 shown in FIG. 18A is displayed. The past fusion image IM1 and the latest fusion image IM1' can display a same anatomical section based on functional abnormality positions included in a region of interest. Thus, by displaying the past and latest fusion images side by side, and at the same time displaying the comparison result display D5, an image-reading doctor can perform follow-up observation of an object based on both images and numerical values. Moreover, since it is possible to perform registration between past and latest fusion images based on anatomical positions included in a region of interest of fusion image, it is possible to perform follow-up observation on the anatomical areas located in the same position.

FIG. 20B shows an example of displaying a superimposed image IM4, in which the past fusion image IM1 and the latest fusion image IM1', which are shown in the upper part of FIG. 20A, are superimposed with each other, on the image display screen W1. The past fusion image and the latest fusion image can be superimposed to be registered with each other based on the functional abnormality positions. In the superimposed image IM4 of FIG. 20B, the region of interest of the past fusion image is shown by a solid line, and the region of interest of the latest fusion image is shown by a broken line. As shown in FIG. 20B, in the superimposed image IM4, the size of the region of interest 1 has decreased. Moreover, it is seen that while the size of the region of interest 2 has decreased, the range of the region of interest has moved upward. Thus, displaying the superimposed image IM4 makes it possible to visually judge progression between past and latest fusion images.

In this way, the medical image display apparatus 100 relating to the present embodiment makes it possible to automatically specify abnormal areas based on anatomical positions from a generated fusion image, and to display the abnormal areas in a list on the display section 40. Such displaying makes it possible to omit the work to specify an anatomical area of an abnormal area from a fusion image, and thus to easily grasp the abnormal area from the fusion image, thereby supporting early diagnosis. Moreover, it is possible to prevent overlooking of abnormal areas, and thereby contribute to high-accuracy diagnosis. Further, it is possible to perform quantitative measurement on abnormal areas and to easily perform follow-up observation on the corresponding abnormal areas based on the anatomical positions. Furthermore, since it is possible to display for comparison abnormal areas at the same anatomical position based on the functional abnormality position, it is possible to easily perform follow-up observation on the past and latest fusion images and make explanations more understandable to the patient and others. Furthermore, it is also possible to contribute to saving of the labor for creating an image-reading report based on abnormal areas specified on a fusion image.

Third Embodiment

The second embodiment is configured, as an example, such that in step ST207, the image fusion section 133 synthesizes functional images acquired at past and latest examinations with a past morphological image, respectively, and generates a past fusion image and a latest fusion image, respectively. Moreover, the medical image display apparatus 100 is configured to perform the processing in and after step ST207, and for example in step ST219, to compare measurement results of past and latest examination data.

In contrast, the third embodiment is configured such that in step ST207, the image fusion section 133 generates a past fusion image and a latest fusion image, respectively, and thereafter the abnormal-area specification section 134 specifies anatomical positions corresponding to respective regions of interest of the past fusion image and the latest fusion image, and displays them in correspondence with the respective fusion images.

Since, in this case, it is possible to perform the processing in and after step ST207 while synchronizing the past and latest fusion images, for example, in the processing in step ST219, it is possible to simultaneously display the past and latest fusion images in a state that the position of the region of interest of the past fusion image is in synchronous with the position of the region of interest of the latest fusion image.

Therefore, since the medical image display apparatus 100 relating to the third embodiment can display side by side, for example, an axial section image of a past fusion image and an axial section image of a present fusion image, and simultaneously display them in a synchronous fashion on the image display screen W1, the user can perform more accurate image reading.

Moreover, the display section 40 of the third embodiment can control page-turning operation such as a rate of display change of a past fusion image and a latest fusion image, and a timing of display change by linking and displaying a past fusion image and a latest fusion image which are anatomically in correspondence with each other based on an anatomical position.

It is noted that in the first to third embodiments, it is possible, for example, to apply a CT image by an X-ray CT apparatus and an MRI image obtained by an MRI apparatus (including a magnetic resonance angiography apparatus) as the morphological image, and also apply a nuclear medicine image obtained from a SPECT apparatus and a PET apparatus as the functional image. The functional image includes images which utilize MRI called fMRI. The fMRI refers to an image which visualizes hemodynamic responses relating to activities of a human brain and spinal cord.

In the above described embodiments, the combination to be applied to the morphological image and functional image is not limited, and for example, a fusion image may be generated by an X-ray CT apparatus and a PET apparatus, or by an MRI apparatus and a SPECT apparatus.

The term of a "processor" or "processing circuitry" as described above includes, for example, a special purpose CPU (Central Processing Unit), a general purpose of CPU, ASIC (Application Specific Integrated Circuit), a PLD (Programmable Logic Device) including a SPLD (Simple Programmable Logic Device) and a CPLD (Complex Programmable Logic Device), and/or FPGA (Field Programmable Gate Array). The "processor" or "processing circuitry" implements the functions or processing as described above by executing one or more programs stored in one or more memories. Further, the functions or the processing described above may be implemented by a single "processor" or "processing circuitry", or may be implemented by plural "processors" or "processing circuitries".

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image display apparatus for displaying at least one medical image acquired from an object, the medical image display apparatus comprising:
    memory circuitry configured to store at least one functional image representing functional information of a tissue in the object, and at least one morphological image representing morphological information of the object;
    processing circuitry configured:
        to specify a region of interest based on the functional image;
        to detect an anatomical position of a characteristic local structure of the object from the morphological image;
        to generate at least one fusion image in which the functional image and the morphological image are superimposed with each other;
        to specify an abnormal area corresponding to the region of interest in the fusion image based on the anatomical position; and
        to specify anatomical area information associated with the anatomical position of the characteristic local structure of the object corresponding to a position of the region of interest as abnormal area information; and
    a display configured to display the abnormal area information together with the region of interest and anatomical area information.

2. The medical image display apparatus according to claim 1, wherein
    the display displays the abnormal area.

3. The medical image display apparatus according to claim 2, wherein the processing circuitry is further configured to generate an abnormal area list, in which the abnormal area corresponding to the region of interest is listed, based on the anatomical position corresponding to the abnormal area, wherein
    the display displays the abnormal area list.

4. The medical image display apparatus according to claim 3, wherein the processing circuitry is further configured
    to compare the abnormal area list of the fusion image acquired in the past on the object with a latest of the abnormal area list of the fusion image acquired on the object, and calculate a comparison result; and
    to generate comparison-result display information from the comparison result, wherein
    the display displays the comparison-result display information.

5. The medical image display apparatus according to claim 4, wherein the processing circuitry is configured to compare a value measured at the measurement section on the fusion image acquired in the past with a value measured at the measurement section on the latest of the fusion image.

6. The medical image display apparatus according to claim 3, wherein the processing circuitry is further configured to specify an image corresponding to the anatomical position selected from among the abnormal area list based on the anatomical position of the fusion image, wherein
    the display displays an image specified in the image specification section.

7. The medical image display apparatus according to claim 6, wherein the processing circuitry is further configured to generate a sequential display image for displaying images specified in the image specification section in an order of the anatomical position listed in the abnormal area list, wherein
    the display displays the sequential display image.

8. The medical image display apparatus according to claim 3, wherein the processing circuitry is further configured to generate a reference-information display item for displaying reference literatures, reference books, medical information, case information relating to the anatomical position listed in the abnormal area list, wherein
    the display displays the reference-information display item.

9. The medical image display apparatus according to claim 2, wherein the processing circuitry is further configured
    to measure an area or volume of the region of interest based on the anatomical position corresponding to the abnormal area; and
    to generate measurement-result display information for each of the abnormal areas from the measured value, wherein
    the display section displays the measurement-result display information.

10. The medical image display apparatus according to claim 2, wherein the processing circuitry is further configured to detect the anatomical position of the characteristic local structure of the object from a plurality of fusion images, and
    the display displays the plurality of fusion images based on the anatomical position of the fusion image.

11. The medical image display apparatus according to claim 10, wherein
    the display synchronizes and displays the plurality of fusion images based on the anatomical position of the fusion image.

12. The medical image display apparatus according to claim 1, wherein
    the area information includes area names.

13. A medical image display system for acquiring and displaying at least one medical image picking up an image of an object over a network, the medical image display system comprising:
    memory circuitry configured to store at least one functional image representing functional information of a tissue in the object, and at least one morphological image representing morphological information of the object;
a processing circuitry configured
to specify a region of interest based on the functional image;
to detect an anatomical position of a characteristic local structure of the object from the morphological image;
to generate at least one fusion image in which the functional image and the morphological image are superimposed with each other;
to specify an abnormal area corresponding to the region of interest in the fusion image based on the anatomical position; and
to specify anatomical area information associated with the anatomical position of a characteristic structure of the object corresponding to the position of the region of interest as abnormal area information; and
a display configured to display the abnormal area information together with the region of interest and anatomical area information.

14. A medical image display apparatus for displaying at least one medical image acquired from an object, the medical image display apparatus comprising:

memory circuitry configured to store at least one functional image representing functional information of a tissue in the object, and at least one morphological image representing morphological information of the object;
processing circuitry configured:
to specify a region of interest based on the functional image;
to detect an anatomical position of a characteristic local structure of the object from the morphological image,
to generate associated data in which the region of interest specified in the functional image data and the anatomical position detected from the morphological image are associated with each other;
to specify an abnormal area corresponding to the region of the interest based on the anatomical position in the associated data; and
to specify anatomical area information associated with the anatomical position of a characteristic local structure of the object corresponding to the position of the region of interest as abnormal area information; and
a display configured to display the abnormal area information together with the region of interest and the anatomical area information.

* * * * *